US012611660B2

(12) United States Patent
    Kang et al.

(10) Patent No.: US 12,611,660 B2
(45) Date of Patent: *Apr. 28, 2026

(54) MOLECULAR SIEVE CIT-16P, ITS SYNTHESIS, TRANSFORMATION AND USE

(71) Applicant: California Institute of Technology, Pasadena, CA (US)

(72) Inventors: Jong Hun Kang, Seoul (KR); Faisal H Alshafei, Monrovia, CA (US); Mark E Davis, Pasenda, CA (US)

(73) Assignee: California Institute of Technology, Pasadena, CA (US)

( * ) Notice: Subject to any disclaimer, the term of this patent is extended or adjusted under 35 U.S.C. 154(b) by 210 days.

This patent is subject to a terminal disclaimer.

(21) Appl. No.: 18/534,042

(22) Filed: Dec. 8, 2023

(65) Prior Publication Data

US 2024/0207831 A1    Jun. 27, 2024

Related U.S. Application Data

(60) Provisional application No. 63/431,151, filed on Dec. 8, 2022.

(51) Int. Cl.
    *B01J 29/85*        (2006.01)
    *B01J 37/00*        (2006.01)
    (Continued)

(52) U.S. Cl.
    CPC ........... *B01J 29/85* (2013.01); *B01J 37/0018* (2013.01); *B01J 37/0045* (2013.01); *B01J 37/04* (2013.01); *B01J 37/06* (2013.01); *B01J*

37/08 (2013.01); *C01B 39/54* (2013.01); *C07C 1/24* (2013.01); *B01J 2229/183* (2013.01);
(Continued)

(58) Field of Classification Search
    CPC .... B01J 29/85; B01J 37/0018; B01J 37/0045; B01J 37/04; B01J 37/06; B01J 37/08; C01B 39/54
    See application file for complete search history.

(56) References Cited

U.S. PATENT DOCUMENTS

| | | | |
|---|---|---|---|
| 2,942,932 A | 6/1960 | Elliott | |
| 3,699,683 A | 10/1972 | Tourtellotte et al. | |

(Continued)

FOREIGN PATENT DOCUMENTS

| | | |
|---|---|---|
| CN | 101632939 A | 1/2010 |
| EP | 0300670 A1 | 1/1989 |

(Continued)

OTHER PUBLICATIONS

Alshafei et al., "Methanol-to-Olefins catalysis on ERI-Type molecular sievess: towards enhancing ethylene selectivity", J. Catal., 2021, 404, 620-633.

(Continued)

*Primary Examiner* — Ellen M McAvoy
(74) *Attorney, Agent, or Firm* — BakerHostetler

(57) ABSTRACT

The disclosure provides a novel silicoaluminophosphate molecular sieve, referred to as CIT-16P, that comprises a silicoaluminophosphate framework with an occluded OSDA that is DiQ-C$_4$ or DiQ-C$_3$. The synthesis of CIT-16P, its conversion to SAPO-17, and the use of the so-derived SAPO-17 in the MTO reaction are also disclosed.

20 Claims, 18 Drawing Sheets

[100]

[010]

[001]

(51) Int. Cl.
  *B01J 37/04* (2006.01)
  *B01J 37/06* (2006.01)
  *B01J 37/08* (2006.01)
  *C01B 39/54* (2006.01)
  *C07C 1/24* (2006.01)

(52) U.S. Cl.
  CPC ...... *C01P 2002/72* (2013.01); *C01P 2002/76*
    (2013.01); *C01P 2002/77* (2013.01); *C01P*
    *2002/85* (2013.01); *C01P 2002/86* (2013.01);
    *C01P 2002/88* (2013.01); *C01P 2004/03*
    (2013.01); *C01P 2006/14* (2013.01)

(56) References Cited

U.S. PATENT DOCUMENTS

| | | | |
|---|---|---|---|
| 4,297,328 | A | 10/1981 | Ritscher et al. |
| 4,544,538 | A | 10/1985 | Zones |
| 4,737,592 | A | 4/1988 | Abrams et al. |
| 4,778,780 | A | 10/1988 | Valyocsik et al. |
| 5,078,979 | A | 1/1992 | Dunne |
| 6,508,860 | B1 | 1/2003 | Kulkarni et al. |
| 9,700,878 | B2 | 7/2017 | Xie et al. |
| 2005/0090390 | A1* | 4/2005 | Venkatathri ............. C01B 37/08 502/214 |
| 2006/0100472 | A1* | 5/2006 | Mertens ................... B01J 29/85 502/208 |
| 2010/0087610 | A1* | 4/2010 | Vaughn .................... B01J 29/85 585/638 |
| 2010/0111828 | A1* | 5/2010 | Pai .......................... C01B 39/54 423/706 |
| 2010/0292071 | A1* | 11/2010 | Ferrini ..................... B01J 29/85 502/55 |
| 2015/0004094 | A1* | 1/2015 | Schmidt ................. B01J 29/041 423/700 |
| 2016/0256860 | A1* | 9/2016 | Zhang ...................... B01J 35/70 |
| 2020/0316572 | A1 | 10/2020 | Shannon et al. |
| 2020/0330966 | A1* | 10/2020 | Petrovic ................... B01J 35/56 |
| 2020/0330973 | A1* | 10/2020 | Lew ........................ B01J 29/047 |

FOREIGN PATENT DOCUMENTS

| | | | | |
|---|---|---|---|---|
| WO | | 97/37763 | A1 | 10/1997 |
| WO | | 01/64340 | A1 | 9/2001 |
| WO | WO-2023218312 | A1 * | 11/2023 | .......... C01B 39/026 |

OTHER PUBLICATIONS

Boultif et al., "Indexing of powder diffraction patterns from low-symmetry lattices by the successive dichotomy method", J. Appl. Cryst., 1991, 24, 987-993.

Boultif et al., "Powder pattern indexing with the dichotomy method", J. Appl. Crystallogr., 2004, 37, 724-731.

Castro et al., "Molecular Modeling, Multinuclear NMR, and diffraction studies in the templated synthesis and characterization of the aluminophosphate molecular sieve STA-2", J. Phys. chem., 2010, 114, 12698-12710.

Chang et al., "Locating structure directing agent and Al in CHA: Combined study of structure determination of X-Ray Powder diffraction and classical lattice energy calculation", Bull Korean Chem. Soc., 2021, 42, 477-482.

Chang et al., "Three-Dimensional crystal structure of novel aluminophosphate PST-5 solved using a powder charge flipping method", RSC Adv., 2017, 7, 38631-38638.

Dahl et al., "On the reaction mechanism for propene formation in the MTO reaction over SAPO-34", Catal. Lett., 1993, 20, 329-336.

Davis, "Ordered porous materials for emerging applications", Nature, 2002, 417, 813-821.

Deem et al., "Framework crystal structure solution by simulated annealing: test application to known zeolite structures", J. Am. Chem. Soc., 1992, 114, 7189-7190.

Deimund et al., "Effect of Heteroatom Concentration in SSZ-13 on the methanol-to-Olefins Reaction", ACS Catal., 2016, 6, 542-550.

Duan et al., "Structural Transformation-Involved Synthesis of Nanosized ERI-Type Zeolite and its catalytic property in the MTO reaction", Inorg. Chem., 2022, 61, 8066-8075.

Dudek et al., "Accurate modeling of the intramolecular electrostatic energy of proteins", Journal of Computational chemistry, 1995, 16, 791-816.

Dusselier et al., "CIT-9: A Fault-Free Gmelinite Zeolite", Angew. Chem., Int. Ed., 2017, 56, 13660-13663.

Dusselier et al., "Small-Pore Zeolites: Synthesis and Catalysis", Chem. Rev., 2018, 118, 5265-5329.

Egan et al., "Mapping aluminum/phosphorus connectives in aluminophosphate glasses", J. Non-Cryst. Solids, 2000, 261, 115-126.

Favre-Nicolin et al., "Free objects for crystallography, a modular approach to ab initio structure determination from powder diffraction", J. Appl. Cryst., 2002, 35, 734-743.

Fenzke et al., "NMR intensity measurements of half-integer quadrupole nuclie", Chem. Phys. Lett., 1984, 111, 171-175.

Gale et al., "GULP: A computer program for the symmetry-adapted simulation of solids", J. chem. soc. Faraday Trans., 1997, 93, 629-637.

Giannozzi et al., "Quantum Espresso: A modular and open-source software project of quantum simulations of materials", Journal of Physics: Condensed Matter, 2009, 21, 395502.

Girard et al., "Computational Prediction of the Phase Transformation of Two As-Synthesized Oxyfluorinated Compounds into the Zeotype CHA Forms", Angew. Chem. Int. Ed., 2002, 41, 972-975.

Kang et al., "Cage-Defining Ring: A Molecular Sieve Structural Indicator for Light Olefin Product Distribution from the Methanol-to-Olefins Reaction", ACS Catal, 2019, 9, 6012-6019.

Kang et al., "Further studies on how the nature of Zeolite Cavities that are bounded by small pores influences the conversion of methanol to light olefins", Chem Phys Chem, 2017, 19, 412-419.

Kang et al., "Transformation of Extra-Large Pore germanosilicate CIT-13 Molecular sieve into extra-large pore CIT-5 Molecular Sieve", Chem. Mater., 2019, 31, 9777-9787.

Kirkpatrick et al., "Optimization by simulated annealing", Science, 1983, 220, 671-680.

Lee et al., "Family of Molecular sieves containing framework-bound organic structure-directing agents", Angew. Chem. Int. Ed., 2015, 54, 11097-11101.

Lee et al., "Solid solution of a zeolite and a framework-bound OSDA-containing molecular sieve", Chem. Sci., 2016, 7, 5805-5814.

Lee et al., "Synthesis and characterization of ERI-Type UZM-12 Zeolites and their methanol-to-olefin performance", J. Am. Chem. Soc., 2010, 132, 12971-12982.

Lok et al., "Silicoaluminophosphate molecular sieves: another new class of microporous crystalline inorganic solids", J. Am. Chem. Soc., 1984, 106, 6092-6093.

Nguyen et al., "Physisorption and chemisorption of Linear Alkenes in Zeolites: A Combined QM-Pot(MP2//BLYP:GULP)—Statistical Thermodynamics Study", J. Phys. Chem. C., 2011, 115, 23831-23847.

Nobel et al., "the templated synthesis and structure determination by synchrotron microcrystal diffraction of the novel small pore magnesium aluminosphate STA-2", J. Chem. Soc. Dalton, Trans., 1997, 4485-4490.

Oszlanyi et al., "Ab initio structure solution by charge flipping", Acta Crystallogr. A, 2004, A60, 134-141.

Park et al., "Structural analysis of Cu/Zeolite with controlled Si/Al ratio and the resulting thermal stability", Catal. today, 2022.

Petricek et al., "crystallographic Computing System JANA2006: General Features", Zeitschift fur kristallographie Crystalline Materials, 2014, 229, 345-352.

Pinilla-Herrero et al., "Complex relationship between SAPO framework topology, content and distribution of Si and catalytic behaviour in the MTO reaction", Catal. Sci. Technolo., 2017, 7, 3892-3901.

Pinilla-Herrero et al., "Effect of framework topology of SAPO catalysts on selectivity and deactivation profile in the methanol-to-olefins reaction", J. Catal., 2017, 352, 54 pages.

(56) References Cited

OTHER PUBLICATIONS

Rodriquez-Carvajal, "Recent advances in magnetic structure determination by neutron powder diffraction", Physica B, 1993, 192, 5569.

Tian et al., "Methanol to Olefins (MTO): From Fundamentals to Commercialization", ACS Catal., 2015, 5, 1922-1938.

Turrina et al., "STA-20: An ABC-6 Zeotype Structure prepared by Co-Templating and Solved via a hypothetical structure database and STEM-ADF Imaging", Chem. Mater., 2017, 29, 2180-2190.

Urzhumtsev et al., "TLS from fundamentals to practice", Crystallography Reviews, 2013, 19, 230-270.

Wilson et al., "Aluminophosphate molecular sieves: a new class of microporous crystalline inorganic solids", J. Am. chem. soc., 1982, 104, 1146-1147.

Winn et al., "TLS parameters to model anisotropic displacements in macromolecular refinement", Acta Crystallogr, 2001, 57, 122-133.

Zibrowisus et al., "Multinuclear MAS NMR study of the microporous alminophosphate AIPO4-17 and the related silicoaluminophosphate SAPO-17", Solid State NMR, 1992, 1, 137-148.

* cited by examiner

[001]

[010]

[100]

S37

S25

S24

S21

S18

S17

S16

S15

AFX Simulated

SAT Simulated 5        10        15        20        25        30        35        40

2θ (degrees)

(c)

(b)

MOLECULAR SIEVE CIT-16P, ITS SYNTHESIS, TRANSFORMATION AND USE

CROSS REFERENCE TO RELATED APPLICATIONS

This application claims the benefit of U.S. Provisional Application No. 63/431,151, filed Dec. 8, 2022, the entirety of which is incorporated by reference herein.

TECHNICAL FIELD

The disclosure pertains to the synthesis and use of a novel silicoaluminophosphate molecular sieve, referred to herein as CIT-16P, that comprises a silicoaluminophosphate framework with an occluded OSDA that is DiQ-$C_4$ or DiQ-$C_3$.

BACKGROUND

Zeolites and related molecular sieves are crystalline microporous materials composed of tetrahedral units ($TO_4$, where T=$Si^{4+}$, $Al^{3+}$, $P^{5+}$, etc.) with pore systems usually smaller than 2 nanometers. Davis, M. E., Ordered porous materials for emerging applications, *Nature* 2002, 417, 813-821. Among them are microporous crystal structures with intracrystalline channels defined by 8-membered-ring (8MR) pore apertures (limited by 8 T-atoms) that are conventionally denoted as 'small-pore' molecular sieves. Dusselier, M.; Davis, M. E., Small-Pore Zeolites: Synthesis and Catalysis, *Chem. Rev.* 2018, 118, 5265-5329. Only molecules and ions smaller than 8MR pores (typically, 3-5 Å), such as light olefins, can diffuse within the channel systems of this class of molecular sieves. The pioneering work on silicoaluminophosphate (SAPO)-type molecular sieves by Flanigen et al. in the 1980s and the commercialization of the methanol-to-olefins (MTO) process thereafter stimulated a wide array of research in synthetic small-pore molecular sieves. See Wilson, S. T., et al. Aluminophosphate molecular sieves: a new class of microporous crystalline inorganic solids, *J. Am. Chem. Soc.* 1982, 104, 1146-1147; Lok, B. M.; et al. Silicoaluminophosphate molecular sieves: another new class of microporous crystalline inorganic solids, *J. Am. Chem. Soc.* 1984, 106, 6092-6093.

Brønsted acid sites in SAPO-based molecular sieves are created by replacing $P^{5+}$ with $Si^{4+}$, resulting in materials with milder acidity than their zeolitic counterparts; thus, the rate of coke formation is effectively attenuated in hydrocarbon-related catalytic reactions such as in the MTO reaction. See Tian, P.; et al. Methanol to Olefins (MTO): From Fundamentals to Commercialization, *ACS Catal.* 2015, 5, 1922-1938. This advantage can then be combined with the ability of small-pore molecular sieves with cages to efficiently retain aromatic hydrocarbon pool intermediates (e.g., methylated benzenes), which act as primary catalytic intermediates for the MTO reaction, to produce product streams rich with small molecules (primarily light olefins). The most successful commercialized MTO catalyst is SAPO-34, having a chabazite (CHA) topology, (see Tian, P.; et al. Methanol to Olefins (MTO): From Fundamentals to Commercialization, *ACS Catal.* 2015, 5, 1922-1938; Dahl, I. M.; Kolboe, S., On the reaction mechanism for propene formation in the MTO reaction over SAPO-34, *Catal. Lett.* 1993, 20, 329-336) which is isostructural to the synthetic zeolite, SSZ-13. See Zones, S. I. Zeolite SSZ-13 and its method of preparation, U.S. Pat. No. 4,544,538. 1985; Deimund, M. A.; et al. Effect of Heteroatom Concentration in SSZ-13 on the Methanol-to-Olefins Reaction, *ACS Catal.* 2016, 6, 542-550. While CHA-type structures have been one of the most investigated frameworks in MTO, various small-pore zeolites and $AlPO_4$-based molecular sieves belonging to other frameworks have also been studied, in an effort to establish correlations between cage structure/geometry and the olefins product distribution. Kang, J. H.; et al. Cage-Defining Ring: A Molecular Sieve Structural Indicator for Light Olefin Product Distribution from the Methanol-to-Olefins Reaction, *ACS Catal.* 2019, 9, 6012-6019; Kang, J. H.; et al. Further Studies on How the Nature of Zeolite Cavities That Are Bounded by Small Pores Influences the Conversion of Methanol to Light Olefins, *ChemPhysChem* 2017, 19, 412-419; Pinilla-Herrero, I.; et al. Effect of framework topology of SAPO catalysts on selectivity and deactivation profile in the methanol-to-olefins reaction, *J. Catal.* 2017, 352, 191-207; Pinilla-Herrero, I.; Márquez-Álvarez, C.; Sastre, E., Complex relationship between SAPO framework topology, content and distribution of Si and catalytic behaviour in the MTO reaction, *Catal. Sci. Technol.* 2017, 7, 3892-3901. It has previously been reported that the olefin selectivities in the MTO reaction over small-pore, cage-type molecular sieves are predominantly influenced by cage topology, and demonstrated that by correlating the cage-defining ring (CDR), a new structural parameter, to the observed olefins product distribution. Kang, J. H.; Alshafei, F. H.; Zones, S. I.; Davis, M. E., Cage-Defining Ring: A Molecular Sieve Structural Indicator for Light Olefin Product Distribution from the Methanol-to-Olefins Reaction, *ACS Catal.* 2019, 9, 6012-6019.

For decades, catalytic 'shape selectivity' in molecular sieves has been a key driver for the discovery of new zeolite structures. In fact, about 60 new molecular sieve structures out of 255 structures enlisted in the IZA database have been reported in the last ten years alone. Many of the newly discovered materials are $AlPO_4$-based molecular sieves, (International Zeolite Association Structure Database (http://america.iza-structure.org/IZA-SC)) such as $AlPO_4$-91 (ANO), $AlPO_4$-78 (AVE), PST-14 (POR), and STA-20 (SWY). Compared to their zeolitic counterparts, structures of $AlPO_4$-based molecular sieves can be more challenging to analyze based on X-ray or electron-beam diffractometry techniques due to their structural instability or complex coordination behaviors of T-sites. For instance, the Al- or P-sites of the $AlPO_4$ framework can form extra coordination bonds with $OH^-/H_2O^{14}$ (Chang, S.; et al. Three-dimensional crystal structure of novel aluminophosphate PST-5 solved using a powder charge flipping method, *RSC Adv.* 2017, 7, 38631-38638) or occluded organic molecules. Lee, J. K.; et al. Solid solution of a zeolite and a framework-bound OSDA-containing molecular sieve, *Chem. Sci.* 2016, 7, 5805-5814. Lee, J. K.; et al. A Family of Molecular Sieves Containing Framework-Bound Organic Structure-Directing Agents, *Angew. Chem. Int. Ed.* 2015, 54, 11097-11101. One such example that demonstrates this difficulty is an organic-$AlPO_4$ hybrid material, PST-5, which transforms to PST-6 (PSI) following the removal of the OSDA. Chang, S.; et al. Three-dimensional crystal structure of novel aluminophosphate PST-5 solved using a powder charge flipping method, *RSC Adv.* 2017, 7, 38631-38638.

The disclosure herein demonstrates the synthesis of a new SAPO material (designated herein as CIT-16P) that transforms into SAPO-17 (ERI) when the OSDA is removed. Diquinuclidinium-based diquats with $C_3$- or $C_4$-linkers, which are OSDAs known to crystallize ERI-, (Alshafei, F. H.; et al. Methanol-to-olefins catalysis on ERI-type molecular sieves: towards enhancing ethylene selectivity, *J. Catal.* 2021, 404, 620-633) AFX-, (Castro, M.; et al. Molecular Modeling, Multinuclear NMR, and Diffraction Studies in the Templated Synthesis and Characterization of the Aluminophosphate Molecular Sieve STA-2, *J. Phys. Chem. C* 2010, 114, 12698-12710) and SAT-type (W. Noble, et al. The templated synthesis and structure determination by synchrotron microcrystal diffraction of the novel small pore magnesium aluminophosphate STA-2, *J. Chem. Soc. Dalton. Trans.* 1997, 4485-4490) molecular sieves, crystallized CIT-16P, albeit in a very narrow range of synthesis parameters. As a result of the OSDA-removal, regardless of the method of organic removal, the structure of the inorganic framework of CIT-16P is transformed into SAPO-17. CIT-16P is structurally related to the recently reported highly disordered framework, ECNU-38P, which also forms ECNU-38, an ERI-type material, by removing its OSDA. See Duan, Z.; et al. Structural Transformation-Involved Synthesis of Nano-sized ERI-Type Zeolite and Its Catalytic Property in the MTO Reaction, *Inorg. Chem.* 2022, 61, 8066-8075. The major structural difference between CIT-16P and ECNU-38P lies in the coordination of the Al-sites. Unlike ECNU-38P, which has a small population of octahedral Al sites, it was revealed that CIT-16P possesses a significant proportion of pentacoordinate Al-sites that condense into tetrahedral sites after the removal of the OSDA cations. The structure solution of the as-synthesized CIT-16P, including the atomic positions of the DiQ-$C_4$ OSDA molecules, demonstrate that the organic cations are tightly bound within vacancies of the inorganic framework of CIT-16P. A SAPO-17 catalyst derived from CIT-16P by thermal treatment shows a longer lifetime with a higher initial methanol conversion in the MTO reaction than ECNU-38 (ERI), likely due to the large crystal size (1-5 μm) of the parent material.

SUMMARY

The disclosure provides a silicoaluminophosphate molecular sieve, referred to as CIT-16P, comprising an occluded OSDA that is DiQ-$C_4$ or DiQ-$C_3$, wherein the CIT-16P is characterized as disclosed herein.

The disclosure also provides methods of making CIT-16P.

The disclosure also provides methods of making SAPO-17 by removing the OSDA from the CIT-16P.

The disclosure also provides SAPO-17 having a low Si/T atom ratio.

The disclosure provides processes for use of the SAPO-17 of the disclosure as a catalyst for the MTO reaction.

SEM image of thermally treated and as-synthesized CIT-16P samples, respectively. (d) Thermogravimetric profile of CIT-16P.

Figure 6:
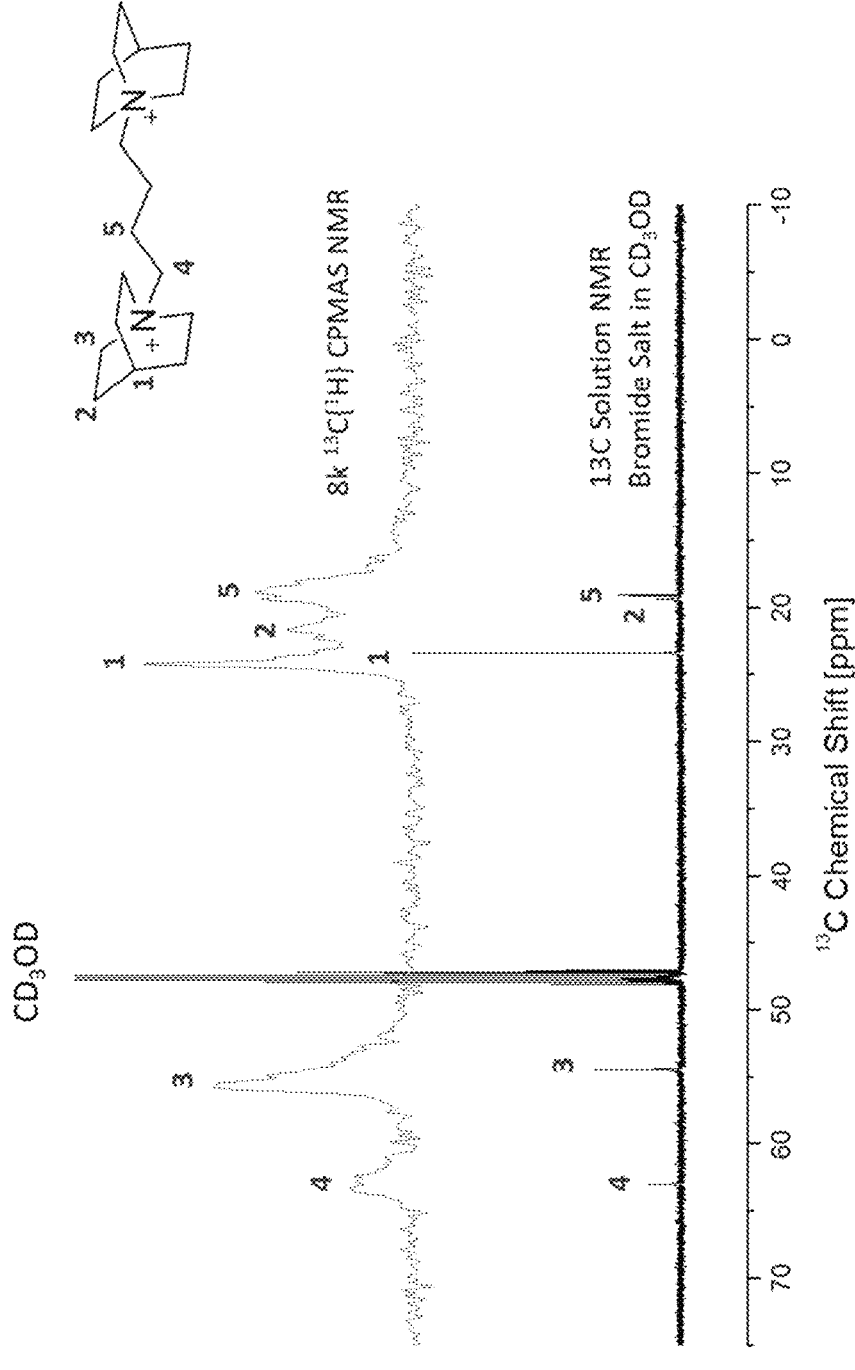

FIG. 6 shows the 8 k MAS solid-state $^{13}$C NMR spectrum of as-made CIT-16P compared to the solution $^{13}$C NMR spectrum of DiQ-$C_4$ OSDA. For the solution NMR spectrum, $CD_3OD$ was used as the solvent.

Figure 5:
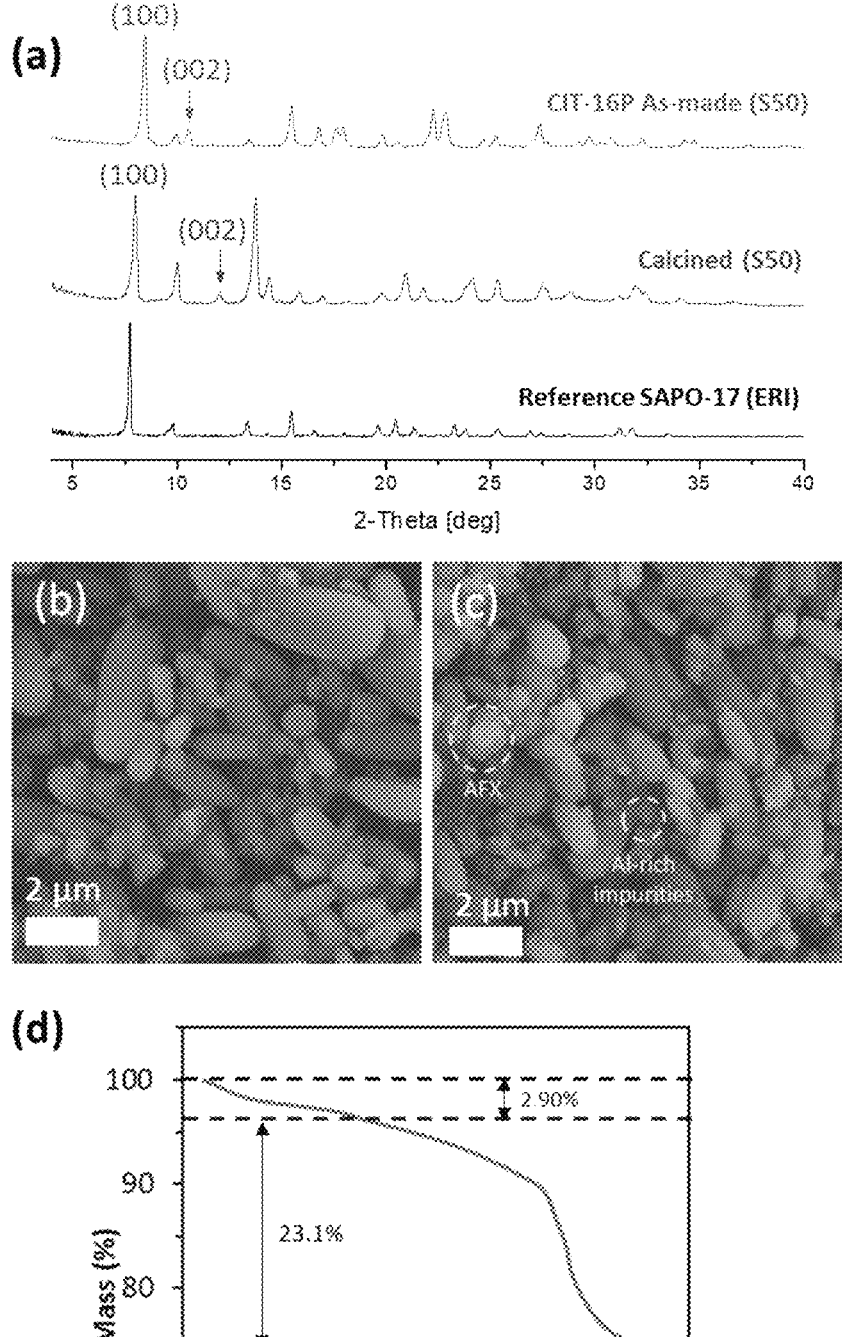
FIG. 5 shows the characterization of the as-synthesized and thermally treated CIT-16P samples (Entry S50 in Table S2). (a) PXRD patterns of as-synthesized and thermally treated CIT-16P compared to the reference SAPO-17. (b, c)
Figure 7:
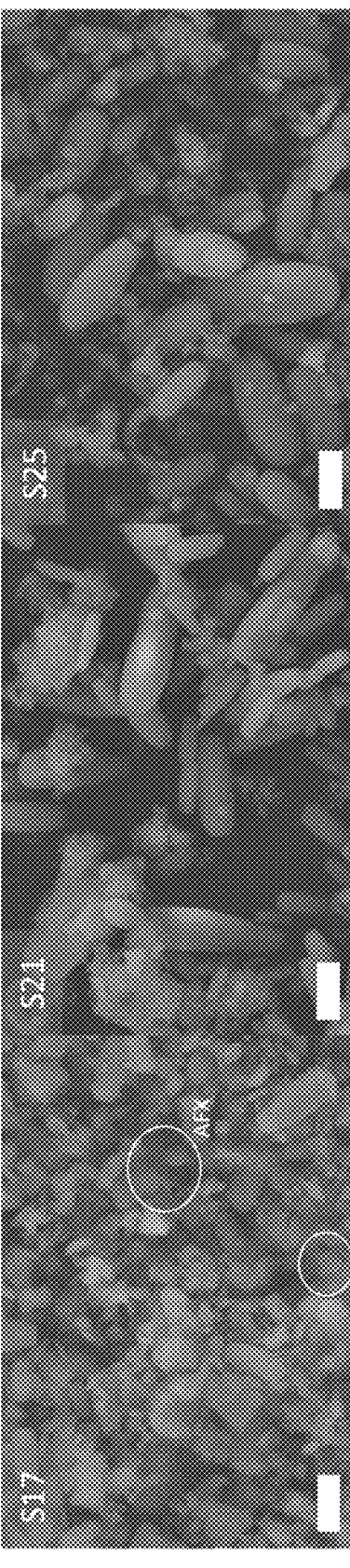

FIG. 7 shows the SEM images at 20 k magnification as of selected CIT-16P samples (from Table S2) (scale bar=2 μm). S17 represents a sample that contained CIT-16P, SAT, and AFX. S21 represents a sample that contained only CIT-16P (with Al-rich regions that are not detectible by XRD). S25 represents a sample that contained CIT-16P and an impurity peak (as shown in FIG. 5).

Figure 8:
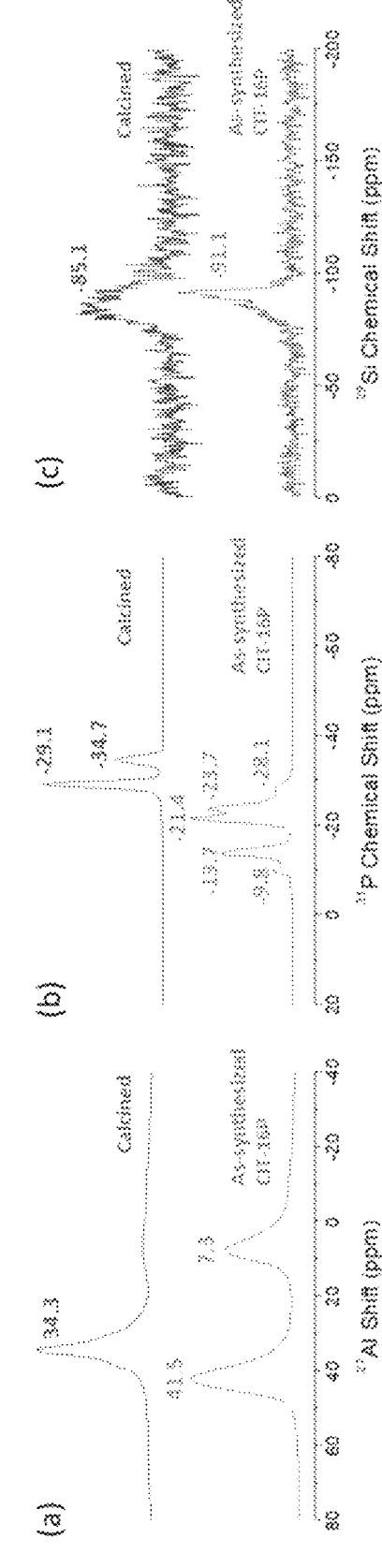

FIG. 8 shows the multinuclear solid-state NMR results of CIT-16P (bottom) and its thermally treated form, SAPO-17 (top): (a) $^{27}$Al MAS, (b) $^{31}$P MAS, and (c) $^1$H-$^{29}$Si CPMAS spectra.

Figure 9:
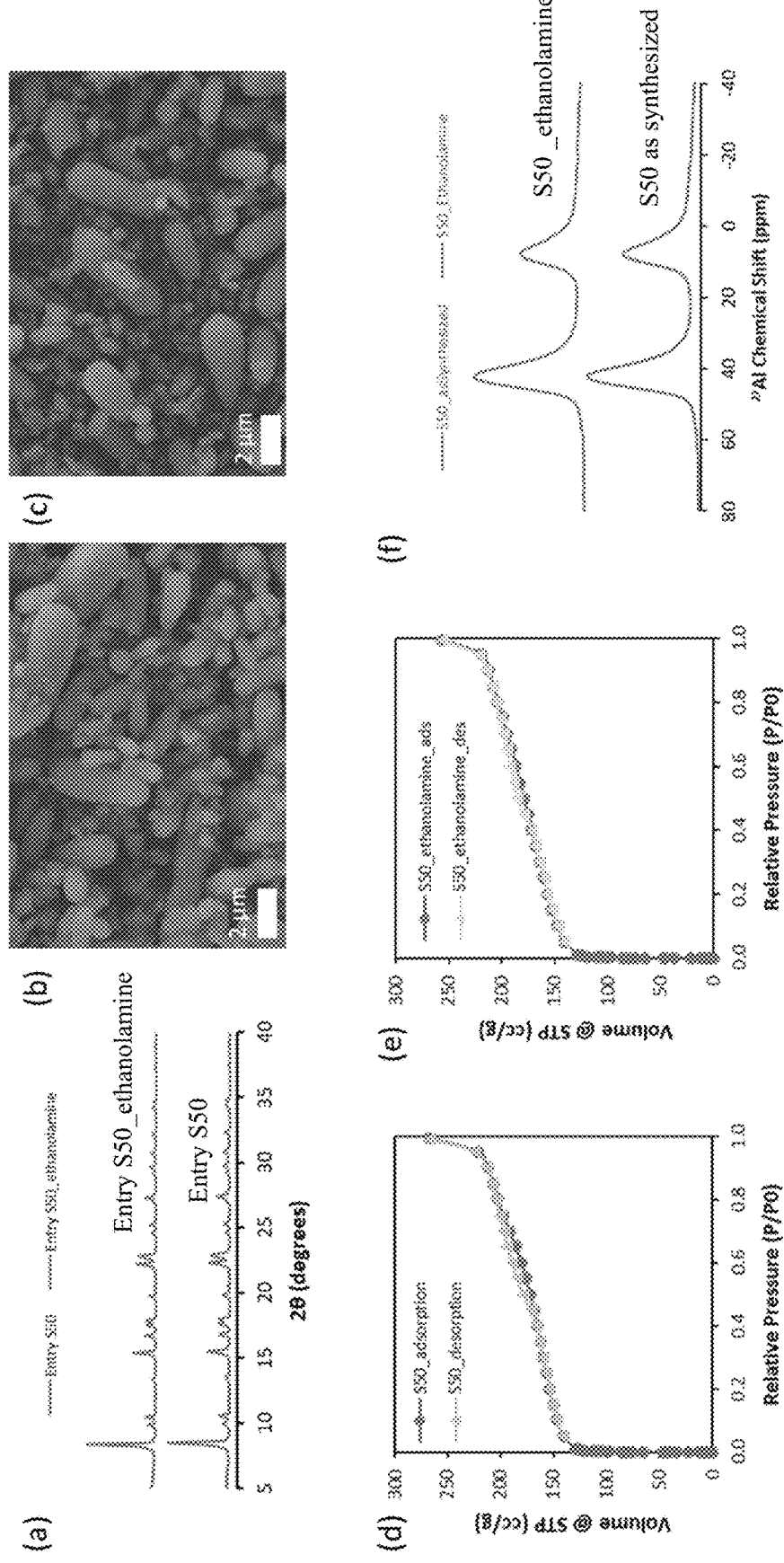

FIG. 9 shows the characterization on the as-synthesized CIT-16P sample (Entry S50 in Table S2) and following treatment with ethanolamine. (a) XRD patterns. (b, c) SEM images of the as-synthesized and treated CIT-16P samples, respectively. (d, e) $N_2$-adsorption-desorption isotherms of the thermally treated CIT-16P (now SAPO-17) and ethanolamine-treated CIT-16P sample (also now SAPO-17). (f) $^{27}$Al MAS NMR spectra.

Figure 10:
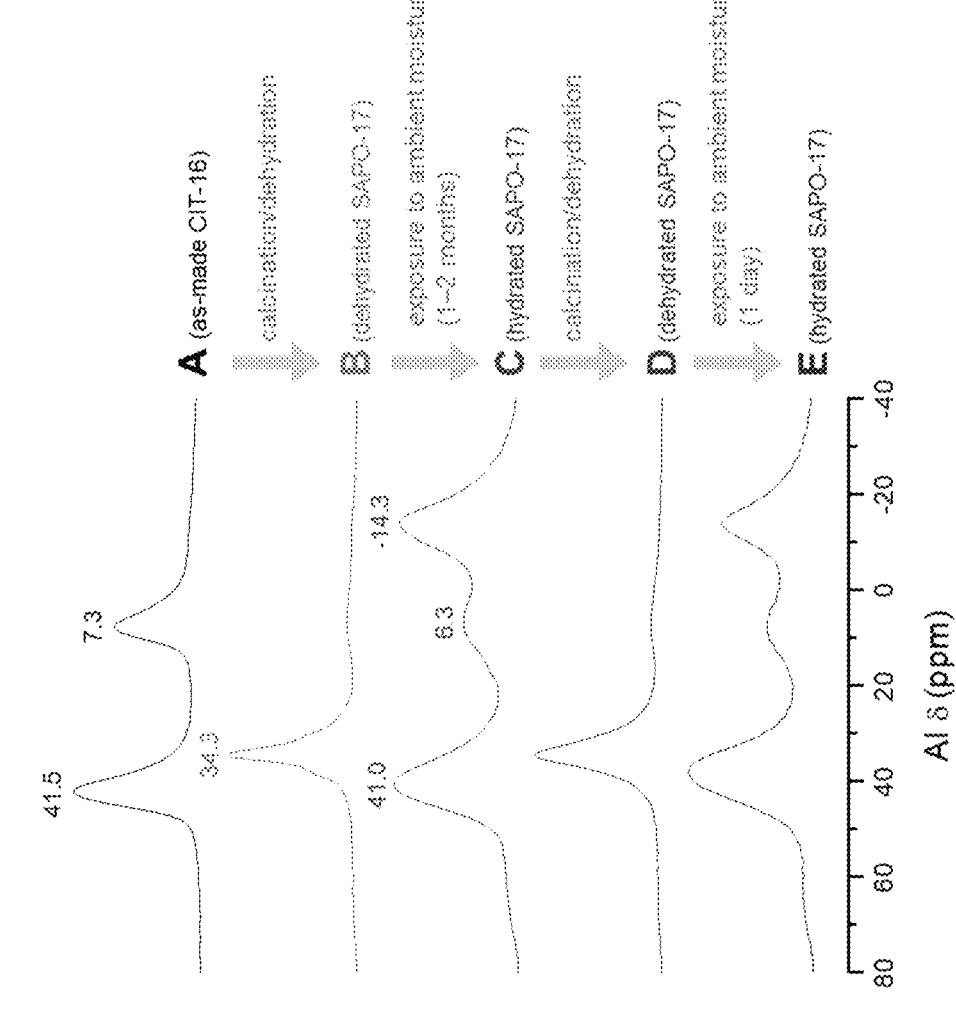

FIG. 10 shows the dehydration-hydration cycle observed based on $^{27}$Al MAS NMR spectroscopy. (A: as-made CIT-16P (Sample=Entry S50) with occluded OSDA, B: the sample freshly calcined and dehydrated, C: the sample after a long exposure (ca. 1-2 months) to ambient moisture, D: the sample after the $2^{nd}$ calcination/dehydration, E: the sample 1 day after the $2^{nd}$ dehydration under ambient moisture).

Figure 11:
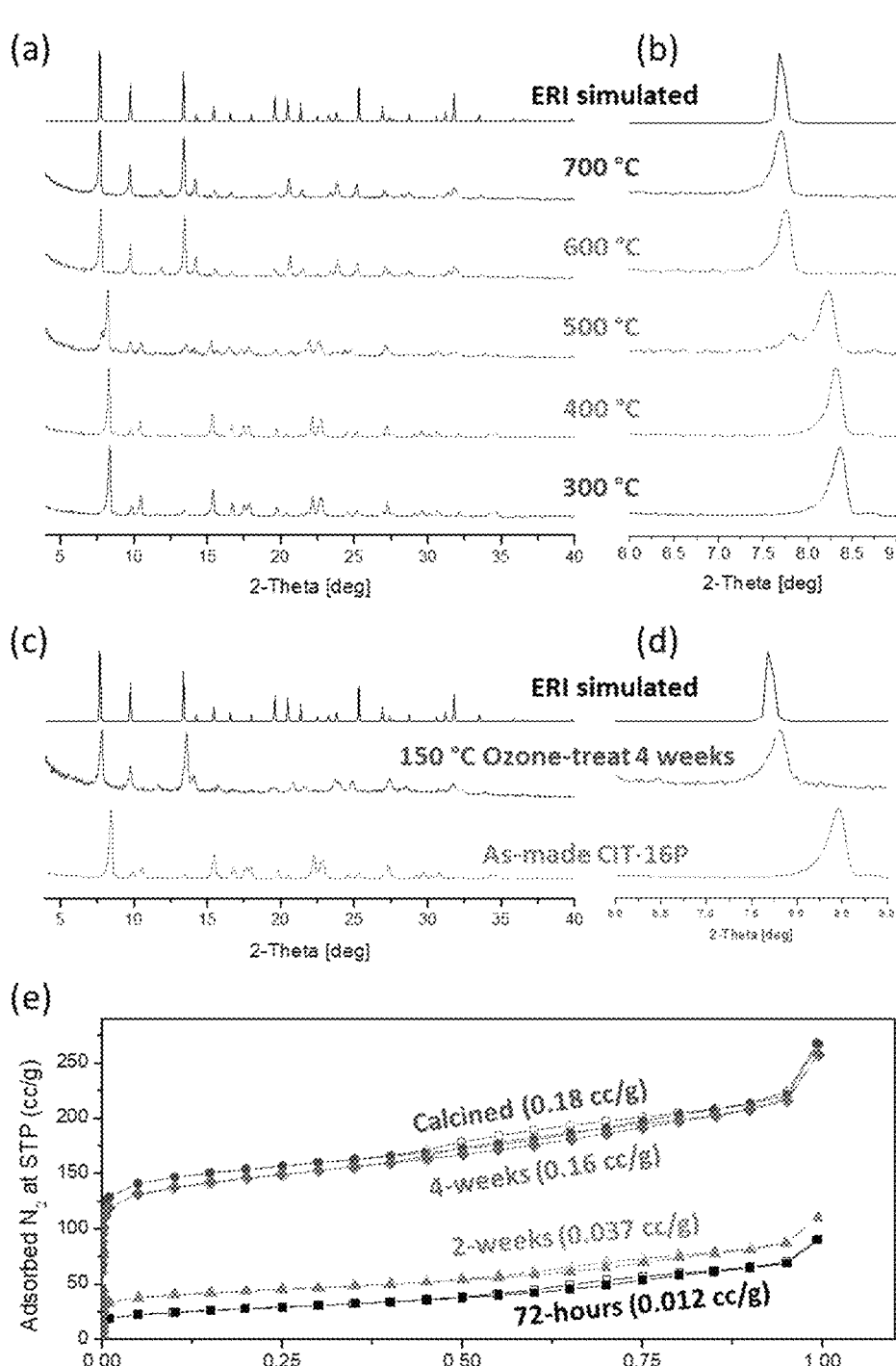

FIG. 11 shows the characterizations of the transformation of CIT-16P to SAPO-17 induced by the removal of the OSDA. (a-b) PXRD profiles of CIT-16P samples after ex-situ heating to elevated temperatures (300-700° C.) displayed in the ranges of (a) 4-40° and (b) 6-9°. (c-d) PXRD profile of a CIT-16P sample before and after the 4-week ozone treatment displayed in the ranges of (c) 4-40° and (d) 6-9°. (e) $N_2$-adsorption-desorption isotherms of the ozone treated CIT-16P sample (Entry S50) compared to the thermally treated one. Treatment time was varied: 72 hours, 2 weeks and 4 weeks.

Figure 12:
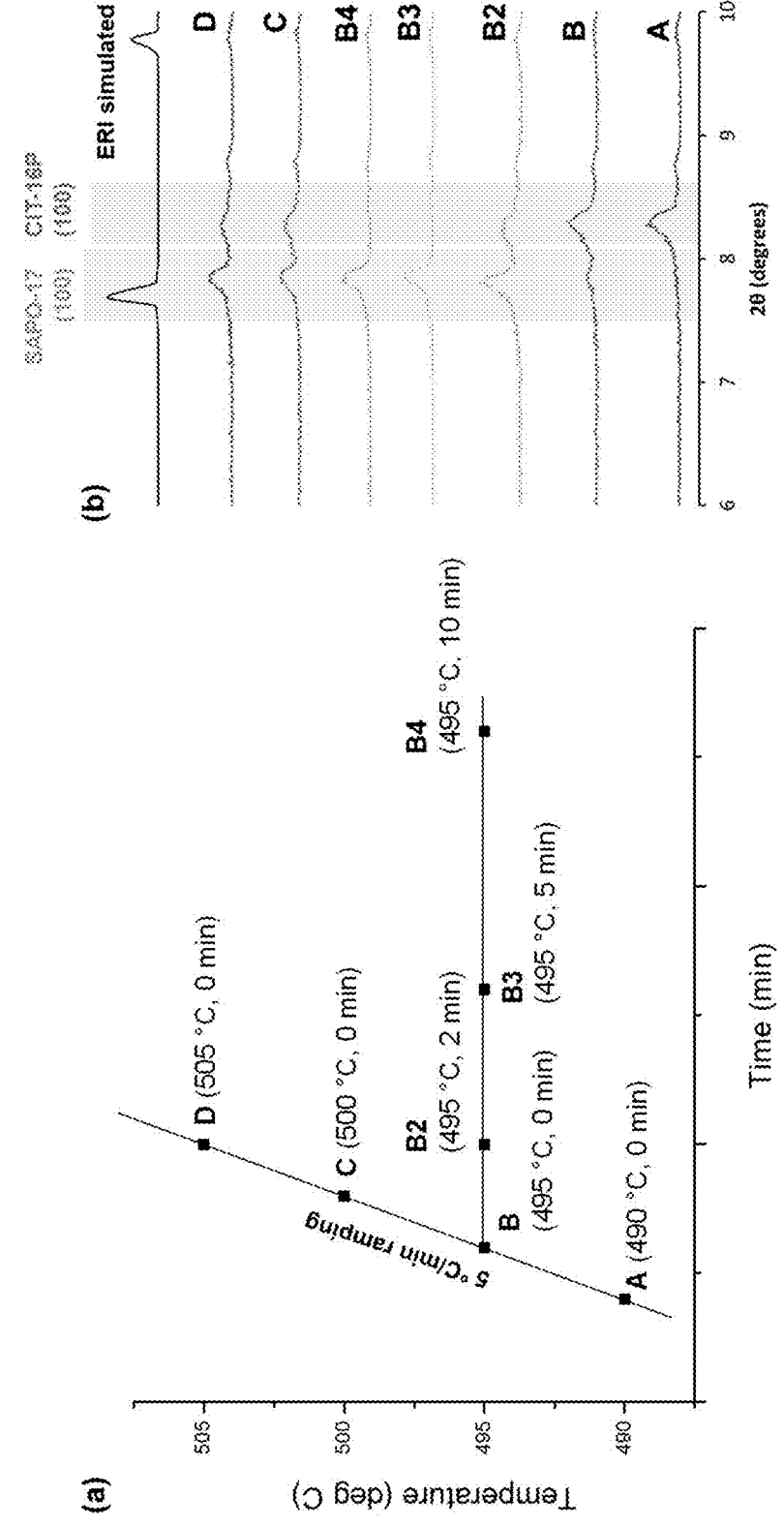

FIG. 12 shows the structural changes of the CIT-16P sample (Entry S50) during ex-situ heating under air. (a) the temperature program associated with the ex-situ heating experiment. Each point denotes the temperature and time at which the sample was quenched. (b) PXRD profiles of samples after the ex-situ heating experiments.

Figure 13:
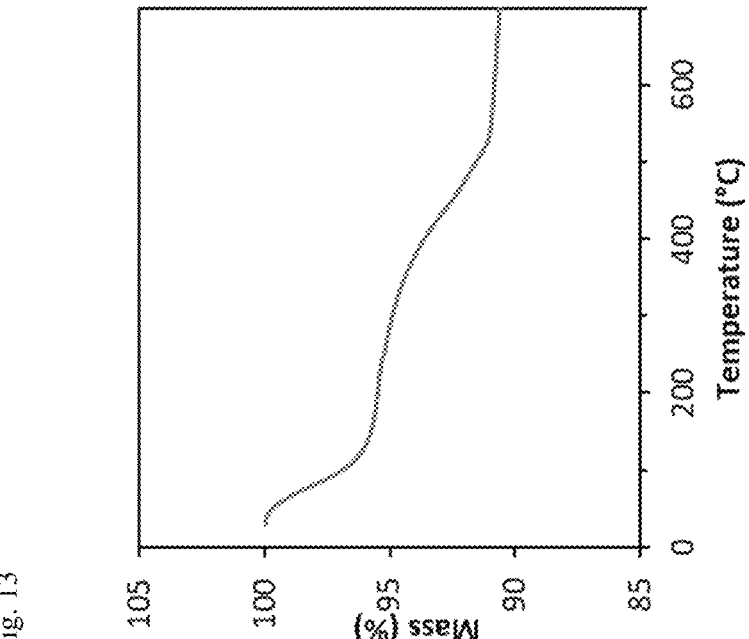

FIG. 13 shows the TGA profile of the CIT-16P sample after 4 weeks of ozone treatment. The amount of OSDA remaining in the sample following 4 weeks of ozone treatment is about 4.8%.

Figure 14:
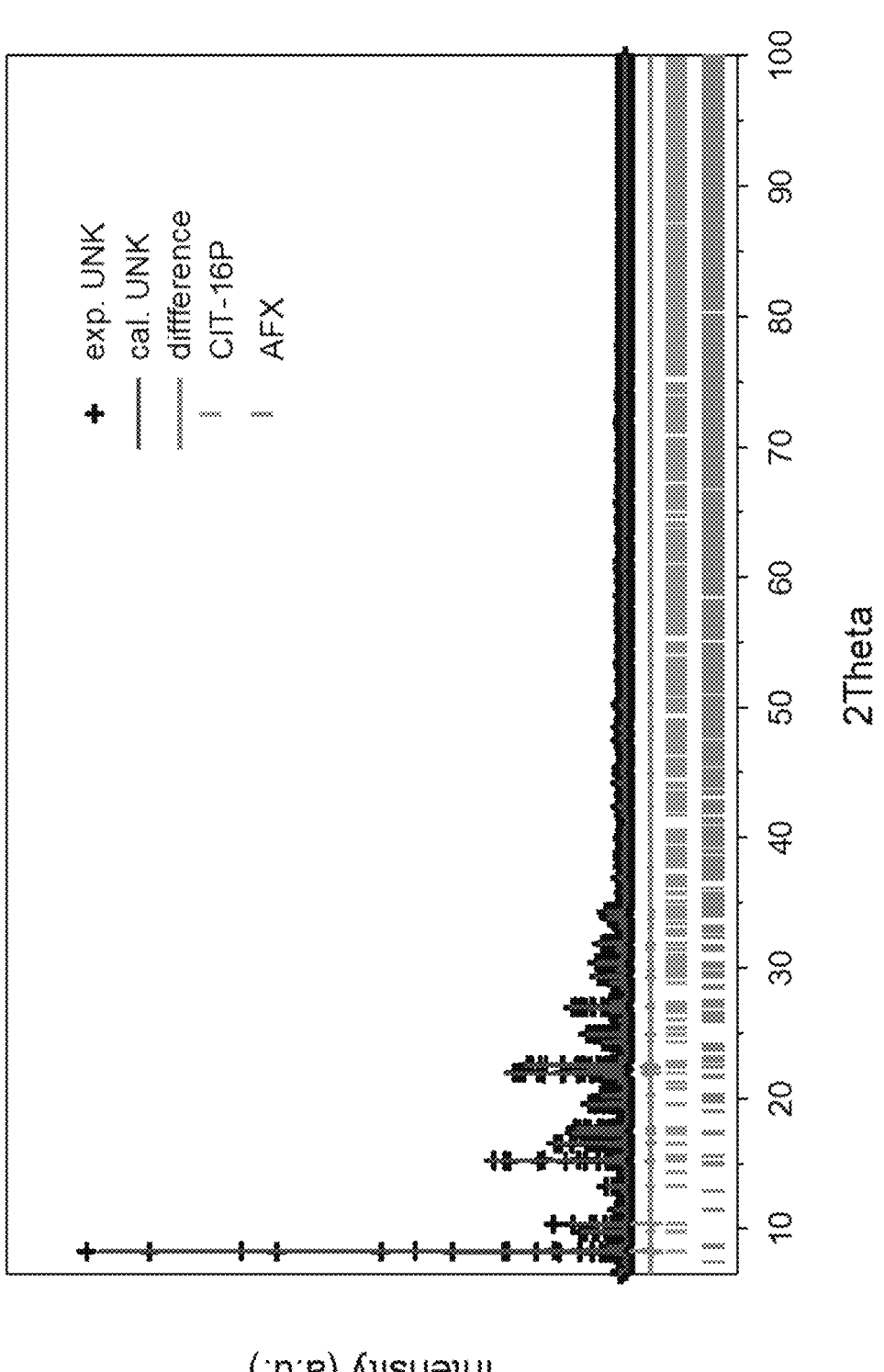

FIG. 14 shows the binary structure refinement for CIT-16P and AFX.

Figure 15:
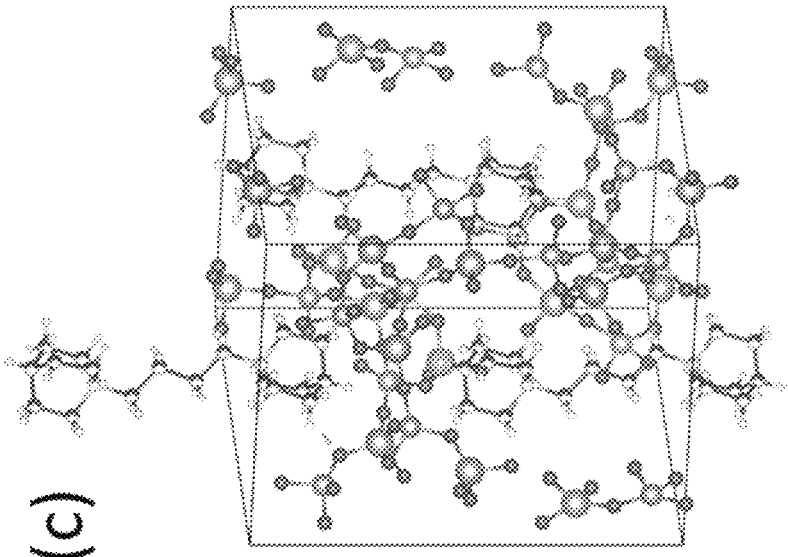
Figure 15:
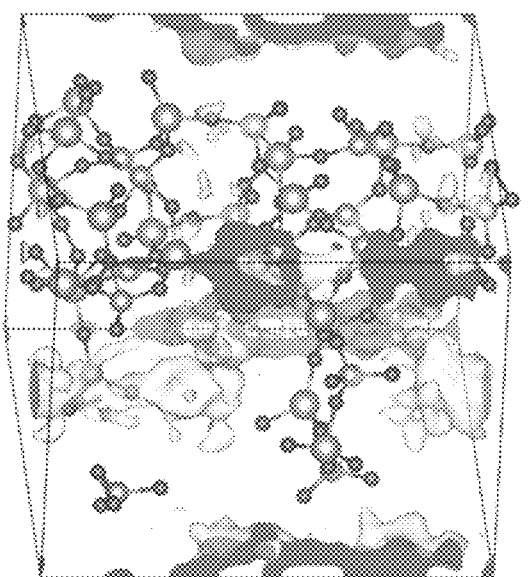

FIG. 15 shows the structure refinement of CIT-16P. (b) electron density map of the OSDA occluded within the CIT-16P cavities. (c) Idealized structure of CIT-16P occluded with DiQ-$C_4$ OSDA dications.

Figure 16:
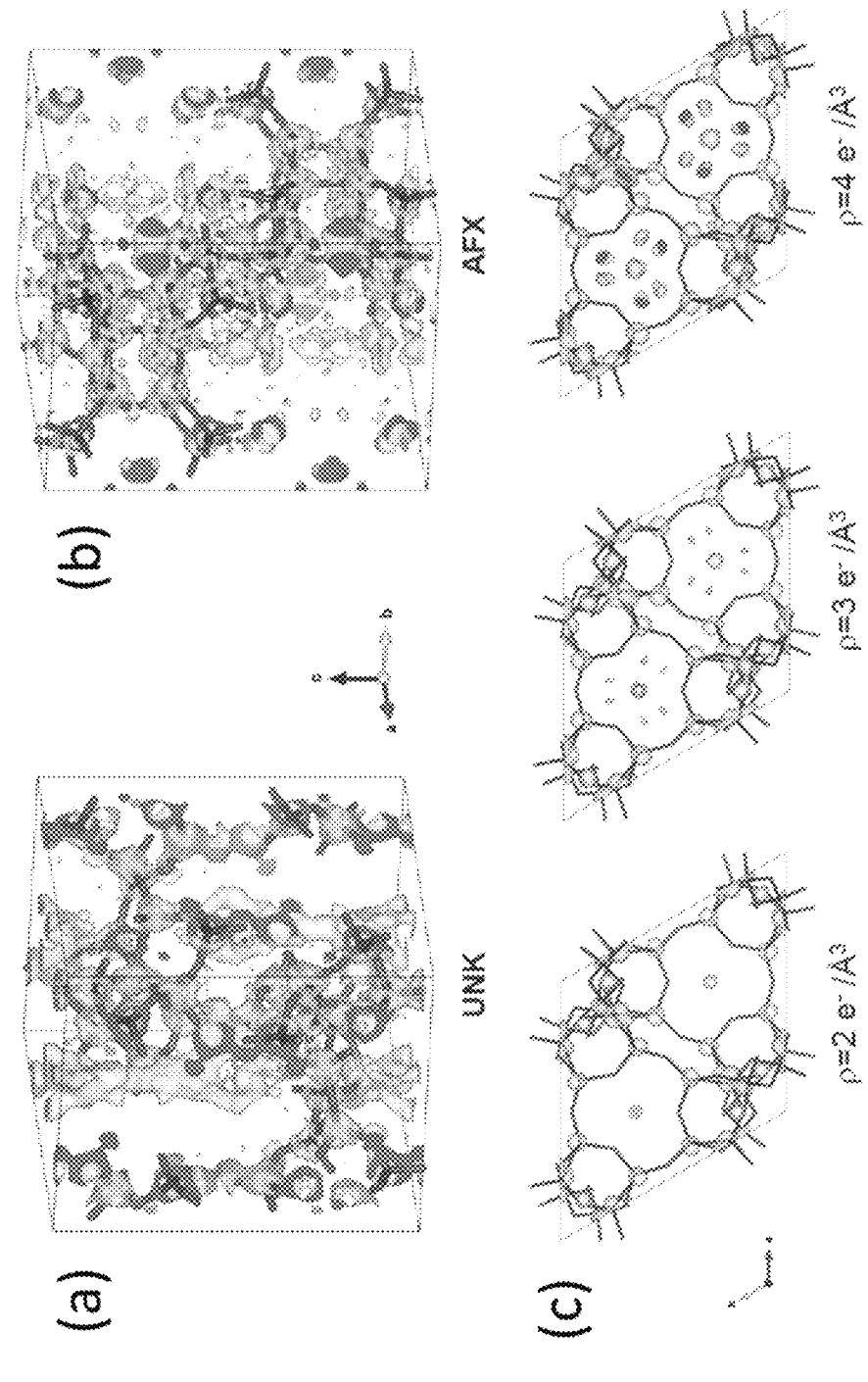

FIG. 16 shows the specification of DiQ-$C_4$ OSDA locations from refinement. Electron density maps of DiQ-$C_4$ OSDA molecules within inorganic frameworks of (a) CIT-16P and (b) AFX. (c) Isopycnic surfaces at different electron densities (2, 3, and 4 e$^-$ Å$^{-3}$) of as-synthesized CIT-16P with the occluded OSDA molecules.

Figure 17:
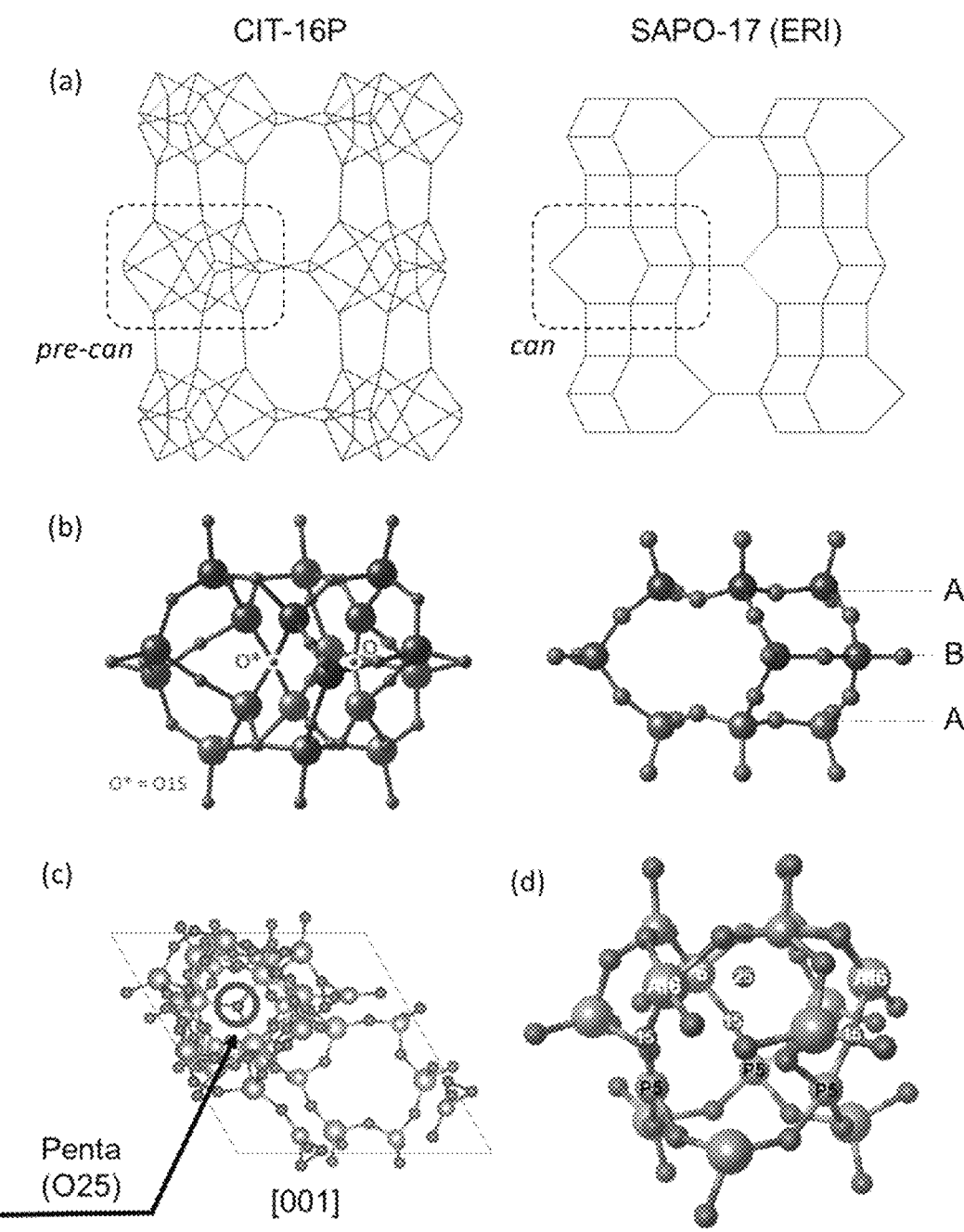

FIG. 17 shows the visualized structural characteristics of CIT-16P reproduced from the binary structure refinement result of CIT-16P and impurity AFX. (a) Wireframe side-views of visualizations of CIT-16P (left) compared to SAPO-17 (ERI) (right). (b) side-views of a pre-can and a can CBU. The top A, middle B, and bottom A layers are denoted in purple, blue, and green colors, respectively. The oxygen site (015) that directly connects the top and bottom layers is highlighted. (c) a top view of a pre-can CBU of CIT-16P revealing the position of the oxygen site (025) that forms pentacoordinated Al-sites. (d) a perspective view that shows the highly-strained T-sites (A16 and P5) of CIT-16P.

Figure 18:
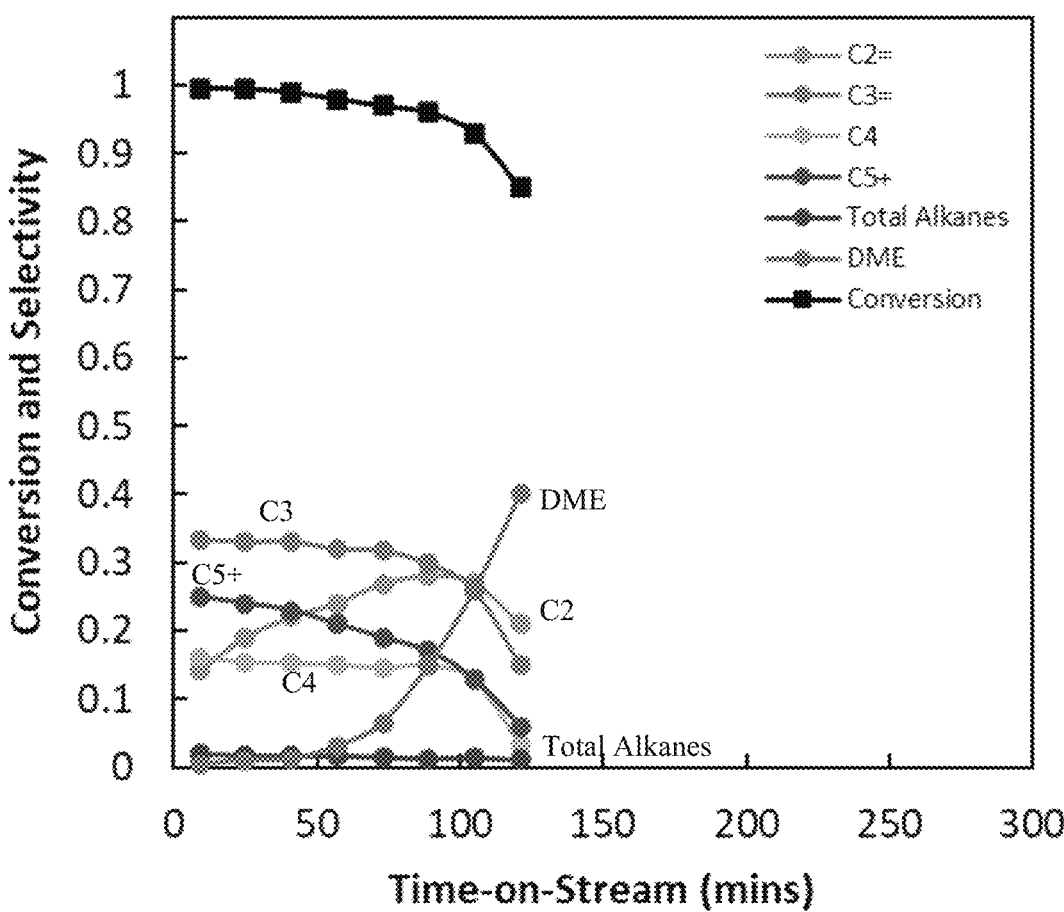

FIG. 18 shows the MTO reaction data obtained at 400° C. and WHSV of 1.3 $h^{-1}$ for SAPO-17 that forms following the transformation of CIT-16P (Entry S50).

DETAILED DESCRIPTION OF ILLUSTRATIVE EMBODIMENTS

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some embodiments, the term "about" as modifying a number indicates the recited number±10% of the recited number. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of."

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C," as separate embodiments.

Throughout this specification, words are to be afforded their normal meaning, as would be understood by those skilled in the relevant art. However, so as to avoid misunderstanding, the meanings of certain terms will be specifically defined or clarified.

The terms "method(s)" and "process(es)" are considered interchangeable within this disclosure.

The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

A material disclosed herein may be referred to as being characterized by graphical data "as shown in" a Figure. Such data include, for example, powder X-ray diffractograms (XRD), thermogravimetric analysis (TGA) profiles, NMR spectra and the like. As is well-known in the art, the graphical data potentially provides additional technical information to further define the respective solid state form which can not necessarily be described by reference to numerical values or peak positions alone. Thus, the term "substantially as shown in" when referring to graphical data in a Figure herein means a pattern that is not necessarily identical to those depicted herein, but that falls within the limits of experimental error or deviations, when considered by one of ordinary skill in the art. The skilled person would readily be able to compare the graphical data in the Figures herein with graphical data generated for an unknown material and confirm whether the two sets of graphical data are characterizing the same material or two different materials.

In some embodiments, PXRD (or XRD) peaks reported herein are measured using $CuK_\alpha$ radiation, $\lambda=1.54$ Å, and are given in degrees 2-θ.

Figure 3:
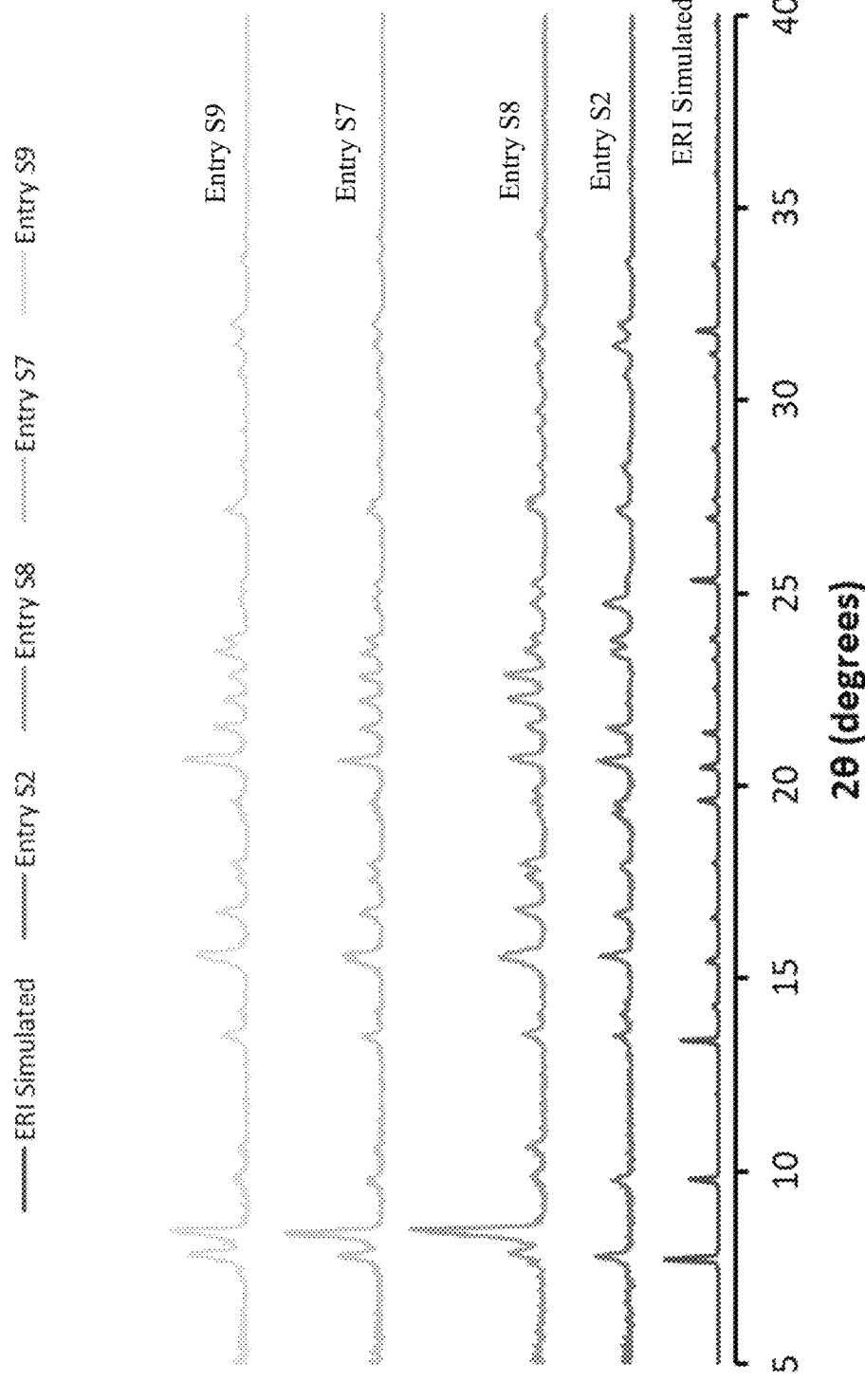
FIG. 3 shows the XRD patterns of the SAPO materials that were synthesized using DiQ-$C_3$—$(OH)_2$ as an OSDA. These results demonstrate the effect of decreasing the OSDA concentration as well as the effect of Si in the gel on the formation of CIT-16P.
Figure 4:
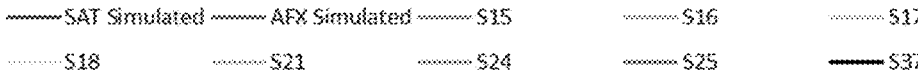
FIG. 4 shows the XRD patterns of the SAPO materials that were synthesized using DiQ-$C_4$—$(OH)_2$ as an OSDA.

In some aspects, the disclosure is directed to a silicoaluminophosphate molecular sieve (referred to herein as CIT-16P) comprising a silicoaluminophosphate framework with an occluded OSDA that is $DiQ-C_4$ or $DiQ-C_3$, and wherein the CIT-16P is characterized by one or more of the following:

a. a PXRD pattern substantially as shown in FIG. 3 entries S7, S8, or S9;

b. a PXRD pattern substantially as shown in FIG. 4, entries S15, S16, S17, S18, S21, S24, S25, or S37;

c. a PXRD pattern substantially as shown in FIG. 5(*a*);

d. PXRD peaks at five or more of: 8.5±0.2, 10.1±0.2, 10.6±0.2, 13.5±0.2, 15.5±0.2, 16.9±0.2, 17.7±0.2, 18.0±0.2, 18.1±0.2, 19.9±0.2, 22.3±0.2, 22.9±0.2, 24.7±0.2, 25.3±0.2, 27.4±0.2, 29.5±0.2, 29.8±0.2, 30.6±0.2, 30.8±0.2, 32.3±0.2, or 34.8±0.2 degrees 2-θ;

e. a thermogravimetric profile substantially as shown in FIG. 5(*d*);

f. a 8 k MAS solid-state $^{13}$C NMR spectrum substantially as shown in FIG. 6;

g. a $^{27}$Al MAS spectrum substantially as shown in FIG. 8(*a*);

h. a $^{27}$Al MAS spectrum having peaks at about 41.5 ppm and about 7.3 ppm;

i. a $^{31}$P MAS spectrum substantially as shown in FIG. 8(*b*);

j. a $^{31}$P MAS spectrum having peaks at about −9.8, −13.7, −21.4, −23.7, and −28.1 ppm;

k. a $^{1}$H-$^{29}$Si CPMAS spectrum substantially as shown in FIG. 8(*c*);

l. a $^{1}$H-$^{29}$Si CPMAS spectrum having peaks at −91.1 ppm;

m. a crystal structure having the lattice parameters shown in Table S4 herein;

n. a crystal structure having the atomic positions and anisotropic tensors of atoms substantially as shown in Table S5 herein;

o. a crystal structure having the topological analysis shown in Table S7; or p. a crystal structure having the bond valences and bond distances substantially as shown in Table S6.

In some embodiments, the CIT-16P is characterized by a PXRD pattern substantially as shown in FIG. 3, entries S7, S8, or S9.

Note here that the relative intensities of the peaks shown in these or any other figures, may be subject to experimental variations, for example due to scanning speed, sample separation, particle size, degree of crystallinity. Such variability is reflected, in part, by any differences in the various PXRD patterns described in the instant application. The person of skill in the art in this area would appreciate the significance of any such variations.

In some embodiments, the CIT-16P is characterized by a PXRD pattern substantially as shown in FIG. 3, entry S7. In other embodiments, the CIT-16P of the disclosure has an x-ray powder diffraction pattern exhibiting peaks at five or more of the peaks shown in FIG. 3, entry S7, ±0.2 degrees 2-θ. In separate embodiments, the composition exhibits six, seven, eight, nine, or ten of the peaks shown in FIG. 3, entry S7, ±0.2 degrees 2-θ.

In some embodiments, the CIT-16P is characterized by a PXRD pattern substantially as shown in FIG. 3, entry S8. In other embodiments, the CIT-16P of the disclosure has an x-ray powder diffraction pattern exhibiting peaks at five or more of the peaks shown in FIG. 3, entry S8, ±0.2 degrees 2-θ. In separate embodiments, the composition exhibits six, seven, eight, nine, or ten of the peaks shown in FIG. 3, entry S8, ±0.2 degrees 2-θ.

In some embodiments, the CIT-16P is characterized by a PXRD pattern substantially as shown in FIG. 3, entry S9. In other embodiments, the CIT-16P of the disclosure has an x-ray powder diffraction pattern exhibiting peaks at five or more of the peaks shown in FIG. 3, entry S9, ±0.2 degrees 2-θ. In separate embodiments, the composition exhibits six, seven, eight, nine, or ten of the peaks shown in FIG. 3, entry S9, ±0.2 degrees 2-θ.

In some embodiments, the CIT-16P is characterized by a PXRD pattern substantially as shown in FIG. 4, entries S15, S16, S17, S18, S21, S24, S25, or S37.

In some embodiments, the CIT-16P is characterized by a PXRD pattern substantially as shown in FIG. 4, entry S15. In other embodiments, the CIT-16P of the disclosure has an x-ray powder diffraction pattern exhibiting peaks at five or more of the peaks shown in FIG. 4, entry S15, ±0.2 degrees 2-θ. In separate embodiments, the composition exhibits six, seven, eight, nine, or ten of the peaks shown in FIG. 4, entry S15, ±0.2 degrees 2-θ.

In some embodiments, the CIT-16P is characterized by a PXRD pattern substantially as shown in FIG. 4, entry S16. In other embodiments, the CIT-16P of the disclosure has an x-ray powder diffraction pattern exhibiting peaks at five or more of the peaks shown in FIG. 4, entry S16, ±0.2 degrees 2-θ. In separate embodiments, the composition exhibits six, seven, eight, nine, or ten of the peaks shown in FIG. 4, entry S16, ±0.2 degrees 2-θ.

In some embodiments, the CIT-16P is characterized by a PXRD pattern substantially as shown in FIG. 4, entry S17. In other embodiments, the CIT-16P of the disclosure has an x-ray powder diffraction pattern exhibiting peaks at five or more of the peaks shown in FIG. 4, entry S17, ±0.2 degrees 2-θ. In separate embodiments, the composition exhibits six, seven, eight, nine, or ten of the peaks shown in FIG. 4, entry S17, ±0.2 degrees 2-θ.

In some embodiments, the CIT-16P is characterized by a PXRD pattern substantially as shown in FIG. 4, entry S18. In other embodiments, the CIT-16P of the disclosure has an x-ray powder diffraction pattern exhibiting peaks at five or more of the peaks shown in FIG. 4, entry S18, ±0.2 degrees 2-θ. In separate embodiments, the composition exhibits six, seven, eight, nine, or ten of the peaks shown in FIG. 4, entry S18, ±0.2 degrees 2-θ.

In some embodiments, the CIT-16P is characterized by a PXRD pattern substantially as shown in FIG. 4, entry S21. In other embodiments, the CIT-16P of the disclosure has an x-ray powder diffraction pattern exhibiting peaks at five or more of the peaks shown in FIG. 4, entry S21, ±0.2 degrees 2-θ. In separate embodiments, the composition exhibits six, seven, eight, nine, or ten of the peaks shown in FIG. 4, entry S21, ±0.2 degrees 2-θ.

In some embodiments, the CIT-16P is characterized by a PXRD pattern substantially as shown in FIG. 4, entry S24. In other embodiments, the CIT-16P of the disclosure has an x-ray powder diffraction pattern exhibiting peaks at five or more of the peaks shown in FIG. 4, entry S24, ±0.2 degrees 2-θ. In separate embodiments, the composition exhibits six, seven, eight, nine, or ten of the peaks shown in FIG. 4, entry S24, ±0.2 degrees 2-θ.

In some embodiments, the CIT-16P is characterized by a PXRD pattern substantially as shown in FIG. 4, entry S25. In other embodiments, the CIT-16P of the disclosure has an x-ray powder diffraction pattern exhibiting peaks at five or more of the peaks shown in FIG. 4, entry S25, ±0.2 degrees 2-θ. In separate embodiments, the composition exhibits six, seven, eight, nine, or ten of the peaks shown in FIG. 4, entry S25, ±0.2 degrees 2-θ.

In some embodiments, the CIT-16P is characterized by a PXRD pattern substantially as shown in FIG. 4, entry S37. In other embodiments, the CIT-16P of the disclosure has an x-ray powder diffraction pattern exhibiting peaks at five or more of the peaks shown in FIG. 4, entry S37, ±0.2 degrees 2-θ. In separate embodiments, the composition exhibits six, seven, eight, nine, or ten of the peaks shown in FIG. 4, entry S37, ±0.2 degrees 2-θ.

In some embodiments, the CIT-16P is characterized by a PXRD pattern substantially as shown in FIG. 5(*a*), entry S50. In other embodiments, the CIT-16P of the disclosure has an x-ray powder diffraction pattern exhibiting peaks at five or more of the peaks shown in FIG. 5(*a*), entry S50, ±0.2 degrees 2-θ. In separate embodiments, the composition exhibits six, seven, eight, nine, or ten of the peaks shown in FIG. 5(*a*), entry S50, ±0.2 degrees 2-θ.

In other embodiments, the CIT-16P of the disclosure exhibits a powder X-ray diffraction (PXRD) pattern exhibiting at five or more of: 8.5±0.2, 10.1±0.2, 10.6±0.2, 13.5±0.2, 15.5±0.2, 16.9±0.2, 17.7±0.2, 18.0±0.2, 18.1±0.2, 19.9±0.2, 22.3±0.2, 22.9±0.2, 24.7±0.2, 25.3±0.2, 27.4±0.2, 29.5±0.2, 29.8±0.2, 30.6±0.2, 30.8±0.2, 32.3±0.2, or 34.8±0.2 degrees 2-θ. In separate embodiments, the composition exhibits six, seven, eight, nine, or ten of the characteristic peaks at 8.5±0.2, 10.1±0.2, 10.6±0.2, 13.5±0.2, 15.5±0.2, 16.9±0.2, 17.7±0.2, 18.0±0.2, 18.1±0.2, 19.9±0.2, 22.3±0.2, 22.9±0.2, 24.7±0.2, 25.3±0.2, 27.4±0.2, 29.5±0.2, 29.8±0.2, 30.6±0.2, 30.8±0.2, 32.3±0.2, or 34.8±0.2 degrees 2-θ.

In other embodiments, the CIT-16P of the disclosure exhibits a powder X-ray diffraction (PXRD) pattern exhibiting peaks at five or more of: 8.5±0.2, 10.1±0.2, 10.6±0.2, 15.5±0.2, 18.0±0.2, 19.9±0.2, 22.3±0.2, 22.9±0.2, or 27.4±0.2, degrees 2-θ. In separate embodiments, the composition exhibits six, seven, eight, or nine of the characteristic peaks at 8.5±0.2, 10.1±0.2, 10.6±0.2, 15.5±0.2, 18.0±0.2, 19.9±0.2, 22.3±0.2, 22.9±0.2, or 27.4±0.2, degrees 2-θ.

In some embodiments, the CIT-16P is characterized by a thermogravimetric profile substantially as shown in FIG. 5(*d*).

In some embodiments, the CIT-16P is characterized by a 8 k CPMAS solid-state $^{13}$C NMR spectrum substantially as shown in FIG. 6.

In some embodiments, the CIT-16P is characterized by a $^{27}$Al MAS spectrum substantially as shown in FIG. 8(*a*). In some embodiments, the CIT-16P is characterized by a $^{27}$Al MAS spectrum having peaks at about 41.5 ppm and about 7.3 ppm.

In some embodiments, the CIT-16P is characterized by a $^{31}$P MAS spectrum substantially as shown in FIG. 8(*b*). In some embodiments, the CIT-16P is characterized by a $^{31}$P MAS spectrum having peaks at about −9.8, −13.7, −21.4, −23.7, and −28.1 ppm.

In some embodiments, the CIT-16P is characterized by a $^{1}$H-$^{29}$Si CPMAS spectrum substantially as shown in FIG. 8(*c*). In some embodiments, the CIT-16P is characterized by a $^{1}$H-$^{29}$Si CPMAS spectrum having peaks at −91.1 ppm.

In some embodiments, the CIT-16P is characterized by a crystal structure having the lattice parameters shown in Table S4 herein.

In some embodiments, the CIT-16P is characterized by a crystal structure having the atomic positions and anisotropic tensors of atoms substantially as shown in Table S5 herein.

In some embodiments, the CIT-16P is characterized by a crystal structure having the topological analysis shown in Table S7 herein.

In some embodiments, the CIT-16P is characterized by a crystal structure having the bond valences and bond distances substantially as shown in Table S6 herein.

In some embodiments, the CIT-16P is characterized by one of the aforementioned characterization parameters. In other embodiments, the CIT-16P is characterized by more than one of the aforementioned characterization parameters.

In some embodiments, the OSDA is DiQ-C$_4$. As used herein, DiQ-C$_4$ refers to a dianion salt of 1,1'-(butane-1,4-diyl)bis(quinuclidin-1-ium):

In some embodiments, DiQ-C$_4$ is used as the dibromide salt. In other embodiments, DiQ-C$_4$ is used as the dihydroxide salt. In yet other embodiments, DiQ-C$_4$ is used as a mixture of the hydroxide and bromide salts.

In other embodiments, the OSDA is DiQ-C$_3$. As used herein, DiQ-C$_3$ refers to a dianion salt of 1,1'-(propane-1,3-diyl)bis(quinuclidin-1-ium):

In some embodiments, DiQ-C$_3$ is used as the dibromide salt. In other embodiments, DiQ-C$_3$ is used as the dihydroxide salt. In yet other embodiments, DiQ-C$_3$ is used as a mixture of the hydroxide and bromide salts.

In some embodiments, the CIT-16P is characterized by the Si/T-atom ratio wherein T=Si+Al+P. The Si/T-atom ratio may be determined by methods known in the art, including, for example, EDS elemental analysis. In some embodiments of the CIT-16P of the disclosure, the Si/T-atom ratio is from about 0.01 to about 0.08, such as for example, about 0.01, 0.02, 0.03, 0.04, 0.05, 0.06, 0.07, or 0.08. In other embodiments of the CIT-16P of the disclosure, the Si/T-atom ratio is from about 0.01 to about 0.04, such as for example, about 0.01, 0.02, 0.03, or 0.04.

In some aspects of the disclosure, the CIT-16P is characterized by its pore volume. In some embodiments, the CIT-16P has a pore volume of less than 0.01 cm$^3$/g.

Processes for Making CIT-16P

In some aspects, the disclosure provides processes for making the CIT-16P molecular sieve. In some embodiments, these processes comprise:

a. preparing a synthesis gel comprising:
    i. water;
    ii. a phosphorus source;
    iii. an aluminum source;
    iv. a silica source; and
    v. an organic structure determining agent (OSDA);
  b. aging the resulting synthesis gel at room temperature;
  c. heating the aged synthesis gel to about 160-200° C.;
  d. washing the resulting CIT-16P powder; and
  e. drying the CIT-16P powder.

In some embodiments of the processes for making the CIT-16P molecular sieve of the disclosure, molar ratio of the components of the synthesis gel is 0.02-0.12 SiO$_2$:0.45-0.50 Al$_2$O$_3$:0.45-0.47 P$_2$O$_5$:0.18-0.40 R(OH)$_2$:30-50 H$_2$O, wherein R=the OSDA which is DiQ-C$_4$ or DiQ-C$_3$.

In some embodiments, the SiO$_2$ in the molar ratio of the components of the synthesis gel is 0.02-0.12, such as, for example, 0.02, 0.03, 0.04, 0.05, 0.06, 0.07, 0.08, 0.09, 0.1, 0.11, or 0.12.

In some embodiments, the $Al_2O_3$ in the molar ratio of the components of the synthesis gel is 0.45-0.50, such as, for example, 0.45, 0.46, 0.47, 0.48, 0.49, or 0.50.

In some embodiments, the $P_2O_5$ in the molar ratio of the components of the synthesis gel is 0.45-0.47, such as, for example, 0.45, 0.46, or 0.47.

In some embodiments, the $R(OH)_2$ in the molar ratio of the components of the synthesis gel is 0.18-0.40, such as, for example, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, or 0.40.

In some embodiments, the $H_2O$ in the molar ratio of the components of the synthesis gel is 30-50, such as, for example, 30, 31, 32, 33, 34, 35, 36, 37, 38, 39, 40, 41, 42, 43, 44, 45, 46, 47, 48, 49, or 50.

In some embodiments of the processes for making the CIT-16P molecular sieve of the disclosure, molar ratio of the components of the synthesis gel is 0.03-0.04 $SiO_2$: 0.47-0.50 $Al_2O_3$:0.45 $P_2O_5$:0.27-0.29 DiQ-$C_4$—(OH)$_2$:40 $H_2O$.

In some embodiments of the processes for making the CIT-16P molecular sieve of the disclosure, molar ratio of the components of the synthesis gel is 0.02-0.12 $SiO_2$:0.45-0.50 $Al_2O_3$:0.45-0.47 $P_2O_5$:0.27-0.40 $R(OH)_2$:30-50 $H_2O$.

In some embodiments of the processes for making the CIT-16P molecular sieve of the disclosure, molar ratio of the components of the synthesis gel is 0.02-0.04 $SiO_2$:0.45-0.50 $Al_2O_3$:0.45-0.47 $P_2O_5$:0.27-0.29 $R(OH)_2$:30-50 $H_2O$.

In some embodiments of the processes for making the CIT-16P molecular sieve of the disclosure, the process comprises:
  a. preparing a synthesis gel by a process comprising:
     i. mixing a phosphorus source and water, and stirring the resulting mixture for 10 minutes;
     ii. adding a aluminum source, and allowing the resulting gel to homogenize for 3-4 hours;
     iii. adding a silica source to the mixture;
     iv. adding an organic structure determining agent (OSDA);
  b. aging the resulting synthesis gel at room temperature for 20-24 hours;
  c. heating the aged synthesis gel to about 160-200° C. for about 1-4 days;
  d. washing the resulting CIT-16P powder;
  e. drying the CIT-16P powder.

In some embodiments of the processes for making the CIT-16P molecular sieve of the disclosure, the process comprises:
  a. preparing a synthesis gel by a process comprising:
     i. mixing phosphoric acid ($H_3PO_4$) (85%) and water, and stirring the resulting mixture for 10 minutes;
     ii. adding aluminum hydroxide, and allowing the resulting gel to homogenize for 3-4 hours;
     iii. adding fumed silica to the mixture;
     iv. adding an organic structure determining agent (OSDA);
  b. aging the resulting synthesis gel at room temperature for 20-24 hours;
  c. heating the aged synthesis gel to about 160-200° C. for about 1-4 days;
  d. washing the resulting CIT-16P powder;
  e. drying the CIT-16P powder.

In some embodiments, the phosphorus source used for making the CIT-16P of the disclosure is phosphoric acid. In other embodiments, the phosphorus source used for making the CIT-16P of the disclosure is $P_2O_5$.

In some embodiments, the aluminum source used for making the CIT-16P of the disclosure is aluminates, alumina, and aluminum compounds such as $AlCl_3$, $Al_2(SO_4)_3$, $Al(OH)_3$, kaolin clays, and other zeolites. In some embodiments, the aluminum source used for making the CIT-16P of the disclosure is aluminum hydroxide.

The silica (silicon oxide) source used in the methods of the disclosure may comprise a silicate, silica hydrogel, silicic acid, fumed silica, colloidal silica, tetra-alkyl orthosilicate, a silica hydroxide or combination thereof. In some embodiments, the silica source used for making the CIT-16P of the disclosure is fumed silica.

In some embodiments of the processes for making the CIT-16P molecular sieve of the disclosure, the OSDA is DiQ-$C_4$.

In some embodiments of the processes for making the CIT-16P molecular sieve of the disclosure, the OSDA is DiQ-$C_3$.

Processes for Making SAPO-17

In some aspects, the disclosure provides processes for making the SAPO-17 by conversion of the disclosed CIT-16P molecular sieve. In such aspects, the SAPO-17 is formed by removal of the occluded OSDA from CIT-16P. In some embodiments, the occluded OSDA is removed from the CIT-16P by heating the CIT-16P to at least 400° C. In other embodiments, the occluded OSDA is removed from the CIT-16P by treating the CIT-16P with ozone.

In some aspects, the disclosure provides processes for making the SAPO-17 by heating the disclosed CIT-16P molecular sieve. In some embodiments, the occluded OSDA is removed from the CIT-16P by heating the CIT-16P to at least 400° C.

In some embodiments of the processes for making SAPO-17, the process comprises heating the CIT-16P at 470-600° C., such as, for example, 470° C., 475° C., 480° C., 485° C., 490° C., 495° C., 500° C., 505° C., 510° C., 515° C., 520° C., 525° C., 530° C., 535° C., 540° C., 545° C., 550° C., 555° C., 560° C., 565° C., 570° C., 575° C., 580° C., 585° C., 590° C., 595° C., or 600° C., to convert the CIT-16P to SAPO-17. In some embodiments of the processes for making the CIT-16P further comprising heating the CIT-16P at 470-600° C., to convert the CIT-16P to SAPO-17.

In some embodiments of the processes for making SAPO-17, the process comprises heating the CIT-16P at about 470-about 600° C., such as, for example, about 470° C., about 475° C., about 480° C., about 485° C., about 490° C., about 495° C., about 500° C., about 505° C., about 510° C., about 515° C., about 520° C., about 525° C., about 530° C., about 535° C., about 540° C., about 545° C., about 550° C., about 555° C., about 560° C., about 565° C., about 570° C., about 575° C., about 580° C., about 585° C., about 590° C., about 595° C., or about 600° C., to convert the CIT-16P to SAPO-17. In some embodiments of the processes for making the CIT-16P further comprising heating the CIT-16P at about 470-about 600° C., to convert the CIT-16P to SAPO-17.

In some embodiments of the processes for making SAPO-17, the process comprises heating the CIT-16P at 490-600° C., such as, for example, 490° C., 495° C., 500° C., 505° C., 510° C., 515° C., 520° C., 525° C., 530° C., 535° C., 540° C., 545° C., 550° C., 555° C., 560° C., 565° C., 570° C., 575° C., 580° C., 585° C., 590° C., 595° C., or 600° C., to convert the CIT-16P to SAPO-17. In some embodiments, the processes for making the CIT-16P further comprise heating the CIT-16P at 490-600° C., to convert the CIT-16P to SAPO-17.

In some embodiments of the processes for making SAPO-17, the process comprises heating the CIT-16P at about 490-about 600° C., such as, for example, about 490° C., about 495° C., about 500° C., about 505° C., about 510° C., about 515° C., about 520° C., about 525° C., about 530° C., about 535° C., about 540° C., about 545° C., about 550° C., about 555° C., about 560° C., about 565° C., about 570° C., about 575° C., about 580° C., about 585° C., about 590° C., about 595° C., or about 600° C., to convert the CIT-16P to SAPO-17. In some embodiments of the processes for making the CIT-16P further comprising heating the CIT-16P at about 490-about 600° C., to convert the CIT-16P to SAPO-17.

In some aspects, the disclosure provides processes for making the SAPO-17 by treating the disclosed CIT-16P with ozone. In some embodiments, the processes for making the CIT-16P further comprise treating the CIT-16P with ozone to convert the CIT-16P to SAPO-17.

In some embodiments, the CIT-16P is treated with ozone at about 150° C. to convert the CIT-16P to SAPO-17.

SAPO-17

In some aspects, the disclosure provides SAPO-17 molecular sieve, produced by a process of the disclosure.

In some embodiments, the SAPO-17 of the disclosure has a Si/T-atom ratio that is less than 0.034 as determined by EDS elemental analysis, wherein T=Si+Al+P, such as, for example, a Si/T-atom ratio that is 0.033, 0.032, 0.031, 0.030, 0.029, 0.028, 0.027, 0.026, 0.025, 0.024, 0.023, 0.022, 0.021, or 0.020.

In some embodiments, the SAPO-17 of the disclosure has a Si/T-atom ratio of 0.022.

In some embodiments, the SAPO-17 of the disclosure has a Si/T-atom ratio of 0.021.

In some embodiments, the SAPO-17 of the disclosure is characterized by a PXRD pattern substantially as shown in FIG. 5(a), entry Calcined (S50). In other embodiments, the SAPO-17 of the disclosure has an x-ray powder diffraction pattern exhibiting peaks at five or more of the peaks shown in FIG. 5(a), entry Calcined (S50), ±0.2 degrees 2-θ. In separate embodiments, the composition exhibits six, seven, eight, nine, or ten of the peaks shown in FIG. 5(a), entry Calcined (S50), ±0.2 degrees 2-θ.

In other embodiments, the SAPO-17 of the disclosure has an x-ray powder diffraction pattern exhibiting peaks at one or more of 8.0±0.2, 10.0±0.2, 12.1±0.2, 13.8±0.2, 14.4±0.2, 21.0±0.2, 24.1±0.2, or 25.3±0.2 degrees 2-θ.

Oxygenate Conversion—Methanol-to-Olefin (MTO) Reaction

In some aspects, the disclosure provides processes for catalytic conversion of a feedstock comprising one or more oxygenates comprising alcohols and ethers to a hydrocarbon product containing light olefins, i.e., $C_2$, $C_3$ and/or $C_4$ olefins. In these aspects, the feedstock is contacted with a SAPO-17 molecular sieve of the disclosure at effective process conditions to produce light olefins. The term "oxygenate" as used herein refers to oxygen-containing compounds such as alcohols, ethers, and carbonyl compounds (e.g., aldehydes, ketones, carboxylic acids). The oxygenate can contain from 1 to 10 carbon atoms, e.g., from 1 to 4 carbon atoms.

In some embodiments, the process is conducted in the presence of one or more diluents which can be present in the oxygenate feed in an amount of from 1 to 99 mole %, based on the total number of moles of all feed and diluent components. Diluents include helium, argon, nitrogen, carbon monoxide, carbon dioxide, hydrogen, water, paraffins, hydrocarbons (such as methane and the like), aromatic compounds, or mixtures thereof.

In some embodiments, the process is conducted in the vapor phase such that the oxygenate feedstock is contacted in a vapor phase in a reaction zone with SAPO-17 molecular sieve of the disclosure at process conditions effective to produce hydrocarbons, i.e., an effective temperature, pressure, WHSV and, optionally, an effective amount of diluent. The process is conducted for a period of time sufficient to produce the desired light olefins. In general, the residence time employed to produce the desired product can vary from seconds to a number of hours. It will be readily appreciated that the residence time will be determined to a significant extent by the reaction temperature, the molecular sieve catalyst, the WHSV, the phase (liquid or vapor) and process design characteristics.

In some aspects, the process is conducted at a wide range of pressures, including but not limited to autogenous pressures and pressures in the range from 0.1 kPa to 10 MPa. In some embodiments, the pressure can be in the range from 7 kPa to 5 MPa, e.g., from 50 kPa to 1 MPa. The foregoing pressures are exclusive of diluents, if any are present, and refer to the partial pressure of the feedstock as it relates to oxygenate compounds and/or mixtures thereof.

In some embodiments, the temperature which can be employed in the oxygenate conversion process can vary over a wide range. In general, the process can be conducted at an effective temperature of from 250° C. to 600° C.

In some aspects, the SAPO-17 molecular sieve of the disclosure can be incorporated into solid particles in which the catalyst is present in an amount effective to promote the desired conversion of oxygenates to light olefins. In one aspect, the solid particles comprise a catalytically effective amount of the catalyst and at least one matrix material such as binder materials, filler materials and mixtures thereof to provide a desired property or properties, e.g., desired catalyst dilution, mechanical strength and the like to the solid particles.

In some aspects, the disclosure provides processes for the production of olefins from a methanol-containing feed comprising passing the methanol-containing feed to a reactor, wherein the reactor comprises a catalyst comprising a SAPO-17 molecular sieve of the disclosure, wherein the reactor is operated at reaction conditions sufficient to generate an effluent stream comprising ethylene and propylene.

In some aspects, the disclosure provides processes for the production of olefins from a methanol-containing feed comprising passing the methanol-containing feed to a reactor, wherein the reactor comprises a catalyst comprising a SAPO-17 molecular sieve of the disclosure, wherein the reactor is operated at reaction conditions sufficient to generate an effluent stream comprising ethylene and propylene in an ethylene to propylene ratio of about 0.66.

In other aspects, the disclosure provides processes for the production of olefins from a methanol-containing feed, the process comprising: passing the methanol-containing feed to a reactor, wherein the reactor comprises a catalyst comprising a SAPO-17 molecular sieve of the disclosure, wherein the reactor is operated at reaction conditions sufficient to generate an effluent stream comprising averaged ethylene, propylene, and $C_4$ selectivities, on a carbon number basis, of 21%, 33%, and 15.2%, respectively, when the methanol conversion is greater than 97%.

In some embodiments, the reactor is a fluidized bed, fixed bed, or swing fixed bed reactor.

In some embodiments of the MTO processes of the disclosure, the reactor is a fluidized bed reactor.

In other embodiments of the MTO processes of the disclosure, the reactor is a fixed bed reactor.

In yet other embodiments of the MTO processes of the disclosure, the reactor is swing fixed bed reactor.

In some embodiments, the process is operated at ambient pressure.

In some aspects of the MTO processes of the disclosure, the methanol-containing feed flow rate provides a weight hourly space velocity (WHSV) of about 0.65 h$^{-1}$ to about 2.6 h$^{-1}$, such as, for example, about 0.65 h$^{-1}$, about 0.7 h$^{-1}$, about 0.75 h$^{-1}$, about 0.8 h$^{-1}$, about 0.85 h$^{-1}$, about 0.9 h$^{-1}$, about 0.95 h$^{-1}$, about 1.0 h$^{-1}$, about 1.05 h$^{-1}$, about 1.1 h$^{-1}$, about 1.15 h$^{-1}$, about 1.2 h$^{-1}$, about 1.25 h$^{-1}$, about 1.3 h$^{-1}$, about 1.35 h$^{-1}$, about 1.4 h$^{-1}$, about 1.45 h$^{-1}$, about 1.5 h$^{-1}$, about 1.55 h$^{-1}$, about 1.6 h$^{-1}$, about 1.65 h$^{-1}$, about 1.7 h$^{-1}$, about 1.75 h$^{-1}$, about 1.8 h$^{-1}$, about 1.85 h$^{-1}$, about 1.9 h$^{-1}$, about 1.95 h$^{-1}$, about 2.0 h$^{-1}$, about 2.05 h$^{-1}$, about 2.1 h$^{-1}$, about 2.15 h$^{-1}$, about 2.2 h$^{-1}$, about 2.25 h$^{-1}$, about 2.3 h$^{-1}$, about 2.35 h$^{-1}$, about 2.4 h$^{-1}$, about 2.45 h$^{-1}$ about 2.5 h$^{-1}$, about 2.55 h$^{-1}$, or about 2.6 h$^{-1}$.

In some aspects of the MTO processes of the disclosure, the methanol-containing feed flow rate provides a weight hourly space velocity (WHSV) of about 0.65 h$^{-1}$ to about 2.6 h$^{-1}$, such as, for example, 0.65 h$^{-1}$, 0.7 h$^{-1}$, 0.75 h$^{-1}$, 0.8 h$^{-1}$, 0.85 h$^{-1}$, 0.9 h$^{-1}$, 0.95 h$^{-1}$, 1.0 h$^{-1}$, 1.05 h$^{-1}$, 1.1 h$^{-1}$, 1.15 h$^{-1}$, 1.2 h$^{-1}$, 1.25 h$^{-1}$, 1.3 h$^{-1}$, 1.35 h$^{-1}$, 1.4 h$^{-1}$, 1.45 h$^{-1}$, 1.5 h$^{-1}$, 1.55 h$^{-1}$, 1.6 h$^{-1}$, 1.65 h$^{-1}$, 1.7 h$^{-1}$, 1.75 h$^{-1}$, 1.8 h$^{-1}$, 1.85 h$^{-1}$, 1.9 h$^{-1}$, 1.95 h$^{-1}$, 2.0 h$^{-1}$, 2.05 h$^{-1}$, 2.1 h$^{-1}$, 2.15 h$^{-1}$, 2.2 h$^{-1}$, 2.25 h$^{-1}$, 2.3 h$^{-1}$, 2.35 h$^{-1}$, 2.4 h$^{-1}$, 2.45 h$^{-1}$ 2.5 h$^{-1}$, 2.55 h$^{-1}$, or 2.6 h$^{-1}$.

In some aspects of the MTO processes of the disclosure, the methanol-containing feed flow rate provides a weight hourly space velocity (WHSV) of 1.3 h$^{-1}$. In some aspects of the MTO processes of the disclosure, the methanol-containing feed flow rate provides a weight hourly space velocity (WHSV) of about 1.3 h$^{-1}$.

In some aspects of the MTO processes of the disclosure, the reactor is operated at a temperature of about 350° C.-about 600° C., such as, for example, about 350° C., about 355° C., about 360° C., about 365° C., about 370° C., about 375° C., about 380° C., about 385° C., about 390° C., about 395° C., about 400° C., about 405° C., about 410° C., about 415° C., about 420° C., about 425° C., about 430° C., about 435° C., about 440° C., about 445° C., about 450° C., about 455° C., about 460° C., about 465° C., about 470° C., about 475° C., about 480° C., about 485° C., about 490° C., about 495° C., about 500° C., about 505° C., about 510° C., about 515° C., about 520° C., about 525° C., about 530° C., about 535° C., about 540° C., about 545° C., about 550° C., about 555° C., about 560° C., about 565° C., about 570° C., about 575° C., about 580° C., about 585° C., about 590° C., about 595° C., or about 600° C.

In some aspects of the MTO processes of the disclosure, the reactor is operated at a temperature of 350° C.-600° C., such as, for example, 350° C., 355° C., 360° C., 365° C., 370° C., 375° C., 380° C., 385° C., 390° C., 395° C., 400° C., 405° C., 410° C., 415° C., 420° C., 425° C., 430° C., 435° C., 440° C., 445° C., 450° C., 455° C., 460° C., 465° C., 470° C., 475° C., 480° C., 485° C., 490° C., 495° C., 500° C., 505° C., 510° C., 515° C., 520° C., 525° C., 530° C., 535° C., 540° C., 545° C., 550° C., 555° C., 560° C., 565° C., 570° C., 575° C., 580° C., 585° C., 590° C., 595° C., or 600° C.

In some aspects of the MTO processes of the disclosure, the reactor is operated at a temperature of about 350° C.-about 400° C., such as, for example, about 350° C., about 355° C., about 360° C., about 365° C., about 370° C., about 375° C., about 380° C., about 385° C., about 390° C., about 395° C., or about 400° C.

In some aspects of the MTO processes of the disclosure, the reactor is operated at a temperature of 350° C.-400° C., such as, for example, 350° C., 355° C., 360° C., 365° C., 370° C., 375° C., 380° C., 385° C., 390° C., 395° C., or 400° C.

In some aspects of the MTO processes of the disclosure, greater than 97% of the methanol in the methanol-containing feed is converted, such as for example, greater than 97%, greater than 97.1%, greater than 97.2%, greater than 97.3%, greater than 97.4%, greater than 97.5%, greater than 97.6%, greater than 97.7%, greater than 97.8%, greater than 97.9%, greater than 98%, greater than 98.1%, greater than 98.2%, greater than 98.3%, greater than 98.4%, greater than 98.5%, greater than 98.6%, greater than 98.7%, greater than 98.8%, greater than 98.9%, greater than 99%, greater than 99.1%, greater than 99.2%, greater than 99.3%, greater than 99.4%, greater than 99.5%, greater than 99.6%, greater than 99.7%, greater than 99.8%, or greater than 99.9%.

In some embodiments of the MTO processes of the disclosure, the catalyst is first pretreated by heating to an elevated temperature, and holding at that temperature for a period of time under flowing air.

In some embodiments of the MTO processes of the disclosure, the catalyst is first pretreated by heating to about 150° C. at 1° C./min, holding for about 3 h, and then heated further to about 580° C. at 1° C./min and holding for about 12 h under flowing air (breathing-grade D).

In some embodiments of the MTO processes of the disclosure, after the catalyst deactivates (as shown by either its conversion drops below 85% or DME selectivity surpasses 50%), the methanol-containing feed is shut off and the catalyst is cooled before being re-activated (air) by heating to an elevated temperature, and holding at that temperature for a period of time under flowing air.

In other embodiments of the MTO processes of the disclosure, after the catalyst deactivates (as shown by either its conversion drops below 85% or DME selectivity surpasses 50%), the methanol-containing feed is shut off and the catalyst is cooled before being re-activated (air) by heating to about 150° C. at 1° C./min, holding for about 3 h, and then heated further to about 580° C. at 1° C./min and holding for about 12 h under flowing air (breathing-grade D).

In other embodiments of the MTO processes of the disclosure, after the catalyst deactivates (as shown by either its conversion drops below 85% or DME selectivity surpasses 50%), the methanol-containing feed is shut off and the catalyst is cooled to approximately 100° C. before being re-activated (air) by heating to an elevated temperature, and holding at that temperature for a period of time under flowing air.

In other embodiments of the MTO processes of the disclosure, after the catalyst deactivates (as shown by either its conversion drops below 85% or DME selectivity surpasses 50%), the methanol-containing feed is shut off and the catalyst is cooled to approximately 100° C. before being re-activated (air) by heating to about 150° C. at 1° C./min, holding for about 3 h, and then heated further to about 580° C. at 1° C./min and holding for about 12 h under flowing air (breathing-grade D).

Other Uses

The SAPO-17 molecular sieves of the disclosure also are useful in other applications, including as an adsorbent for gas separations; as a catalyst for making small amines; to reduce oxides of nitrogen in a gas streams, such as automobile exhaust; as a cold start hydrocarbon trap in combustion engine pollution control systems; and for trapping C$_3$ fragments.

17

18

Gas Separation

The SAPO-17 molecular sieves of the disclosure can be used to separate gases. For example, they can be used to separate carbon dioxide from natural gas. Typically, the molecular sieve is used as a component in a membrane that is used to separate the gases. Examples of such membranes are disclosed in U.S. Pat. No. 6,508,860.

Synthesis of Amines

The SAPO-17 molecular sieves of the disclosure can be used in a catalyst to prepare methylamine or dimethylamine. Dimethylamine is generally prepared in industrial quantities by continuous reaction of methanol (and/or dimethyl ether) and ammonia in the presence of a silica-alumina catalyst. The reactants are typically combined in the vapor phase, at temperatures of from 300° C. to 500° C., and at elevated pressures. Such a process is disclosed in U.S. Pat. No. 4,737,592.

Reduction of Oxides of Nitrogen (NOx)

The SAPO-17 molecular sieves of the disclosure can be used for the catalytic reduction of the oxides of nitrogen in a gas stream. Typically, the gas stream also contains oxygen, often a stoichiometric excess thereof. Also, the molecular sieve can contain a metal or metal ions within or on it which are capable of catalyzing the reduction of the nitrogen oxides. Examples of such metals or metal ions include lanthanum, chromium, manganese, iron, cobalt, rhodium, nickel, palladium, platinum, copper, zinc, and mixtures thereof. See, e.g., U.S. Pat. No. 4,297,328.

Treatment of Engine Exhaust (Cold Start Emissions)

The SAPO-17 molecular sieves of the disclosure can also be used in adsorbent beds to adsorb the hydrocarbons during the cold start portion of the engine. Although the process typically will be used with hydrocarbon fuels, the present disclosure can also be used to treat exhaust streams from alcohol-fueled engines. The adsorbent bed is typically placed immediately before the catalyst. Thus, the exhaust stream is first flowed through the adsorbent bed and then through the catalyst. The adsorbent bed preferentially adsorbs hydrocarbons over water under the conditions present in the exhaust stream. After a certain amount of time, the adsorbent bed has reached a temperature (typically about 150° C.) at which the bed is no longer able to remove hydrocarbons from the exhaust stream. That is, hydrocarbons are actually desorbed from the adsorbent bed instead of being adsorbed. This regenerates the adsorbent bed so that it can adsorb hydrocarbons during a subsequent cold start. The use of adsorbent beds to minimize hydrocarbon emissions during a cold start engine operation is known in the art. See, for example, U.S. Pat. Nos. 2,942,932; 3,699,683; and 5,078,979.

In some embodiments, the engine exhaust gas stream which is to be treated is flowed over a molecular sieve bed comprising SAPO-17 molecular sieves of the disclosure as a first exhaust stream. The first exhaust stream which is discharged from the molecular sieve bed is now flowed over a catalyst to convert the pollutants contained in the first exhaust stream to innocuous components and provide a treated exhaust stream which is discharged into the atmosphere. It is understood that prior to discharge into the atmosphere, the treated exhaust stream can be flowed through a muffler or other sound reduction apparatus well known in the art.

When the molecular sieve bed reaches a sufficient temperature, typically from 150° C. to 200° C., the pollutants which are adsorbed in the bed begin to desorb and are carried by the first exhaust stream over the catalyst. At this point the catalyst has reached its operating temperature and is therefore capable of fully converting the pollutants to innocuous components. Exemplary uses of molecular sieves in this manner are given in U.S. Pat. No. 9,700,878.

EXAMPLES

Chemicals and Materials

All chemicals were used as-received without further purification: quinuclidine (97%, Alfa Aesar), 1,3-dibromopropane (99%, Sigma-Aldrich), 1,4-dibromobutane (99%, Sigma-Aldrich), diethyl ether (98%, VWR), acetone (99.5%, Sigma-Aldrich), acetone (Fisher), methanol (99.9%, Sigma-Aldrich), DOWEX™ Monosphere™ 550A hydroxide ion-exchange resin (Dow Chemical), deuterium oxide (D, 99.9%, Cambridge Isotope Laboratories, Inc.), methanol-$d_4$ (99 atom % D, Sigma-Aldrich), dichloromethane-$d_2$ (99.5 atom % D, Aldrich), ethanolamine (99.5%, Sigma-Aldrich), phosphoric acid (85%, MACRON), hydrated alumina (Reheis F2000), aluminum hydroxide gel (Barcroft™ 0250, SPI Pharma), pseudoboehmite (Catapal B, VISTA), aluminum hydroxide (Pfaltz and Bauer), fumed silica (Cab-O-Sil®, ACROS), and hydrofluoric acid (48 wt %, Sigma Aldrich). The moisture contents of the solid sources involved in synthesis were determined by temperature-gravimetric analysis (TGA).

Synthesis of the Organic Structure-Directing Agents (OSDAs)

Bisquinuclidinium-butane (DiQ-$C_4$)

Figure 1:
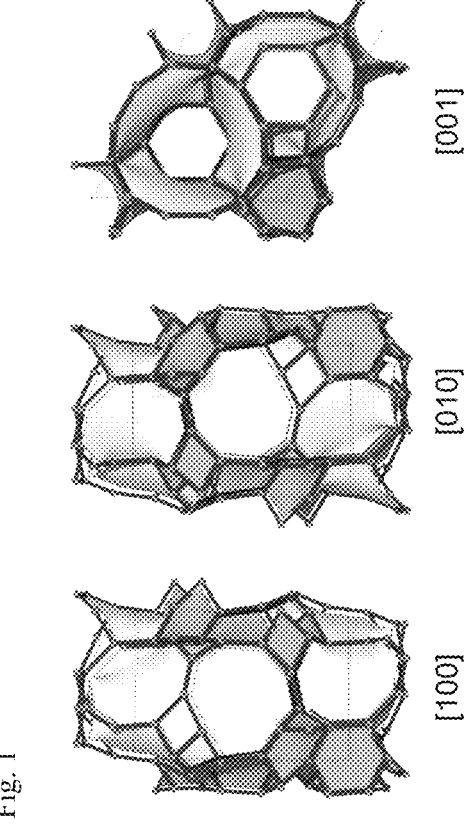
FIG. 1 shows the natural tiling of the idealized CIT-16P structure refined in the space group P6$_3$22.
Figure 2:
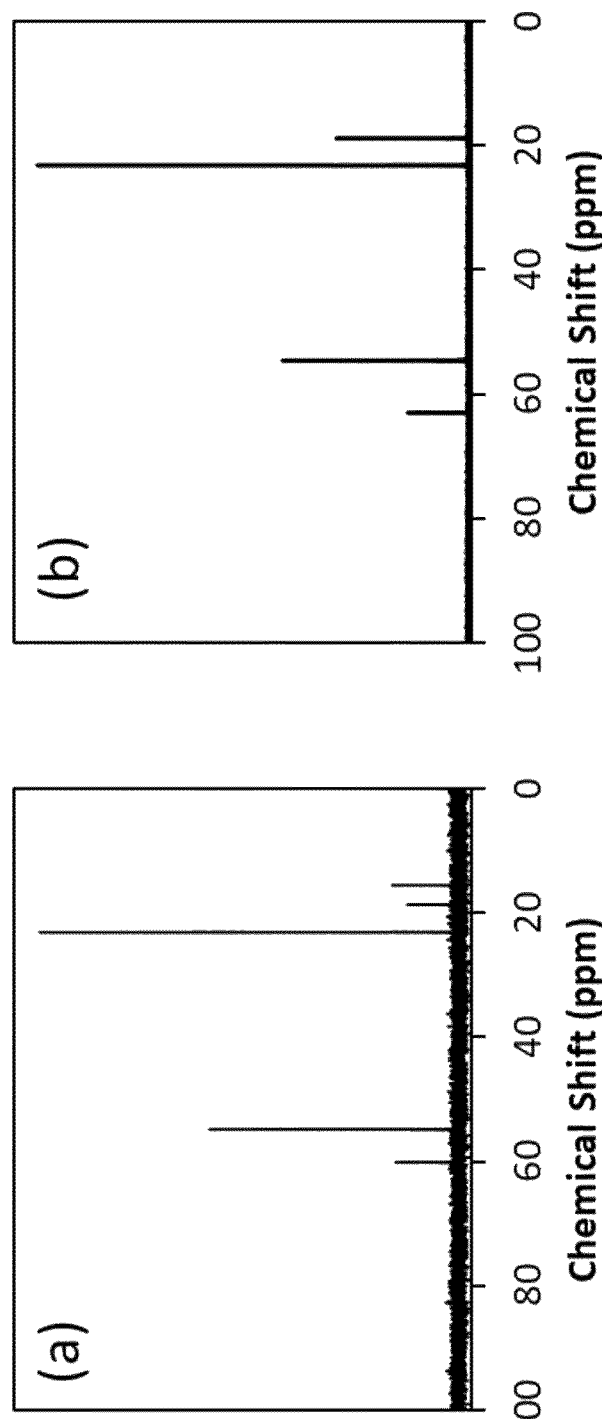
FIG. 2 shows the $^{13}$C-NMR of the OSDAs used in this work in their bromide form: (a) DiQ-$C_3$ and (b) DiQ-$C_4$. The OSDAs were dissolved in $D_2O$ for (a) and (b).

DiQ-$C_4$ was prepared from the reaction of quinuclidine and 1,4-dibromobutane. In a typical synthesis, quinuclidine (100 mmol) was mixed with 150 cm$^3$ of methanol and stirred at room temperature for a few minutes. The solution was then heated to 45° C. in an oil bath. After reaching 45° C., 1,4-dibromobutane (35 mmol) was added dropwise to the quinuclidine-containing solution while stirring. After adding 1,4-dibromobutane, the reaction mixture was heated to 80° C. and refluxed for 6 days. Methanol was then evaporated using a rotary evaporator, and the solid product was filtered and washed with copious amounts of methanol, diethyl ether, and acetone. Following this, the solid was dried under vacuum at room temperature for 6-8 h. The $^{13}$C NMR spectrum of DiQ-$C_4$ OSDA in its bromide form is shown in FIG. 2.

The OSDA was then converted to its hydroxide form, and its concentration was determined by titration. The OSDA above was first ion-exchanged into its hydroxide form by dissolving the organic salt in DI water and then adding DOWEX™ Monosphere™ 550A hydroxide ion-exchange resin. Specifically, for every 100 mmol of OSDA in the halide form, approximately 300 cm$^3$ (by volume) of resin and 500 cm$^3$ of DI water were added. The mixture was then stirred for 24 h at room temperature. After 24 h, the resin was separated by filtration, and the process was repeated a second time. The concentration of the OSDA, now in the hydroxide form, was quantified using a Mettler Toledo DL22 Potentiometric pH meter. Five readings were taken for each OSDA concentration, and these values were then averaged and used for gel calculations.

Bisquinuclidinium-propane (DiQ-$C_3$)

DiQ-$C_3$ was prepared similarly to the DiQ-$C_4$ OSDA outlined above, with the only differences being the solvent used and the use of 1,3-dibromopropane. Instead of methanol, acetone was used as a solvent for the synthesis of DiQ-$C_3$. The $^{13}$C NMR spectrum of DiQ-$C_3$ OSDA in its bromide form is also shown in FIG. 2.

Synthesis of SAPO CIT-16P

The following gel composition was examined for the synthesis of CIT-16P-type molecular sieves: $0.02\text{-}0.12 \text{SiO}_2$: $0.45\text{-}0.50 \text{ Al}_2\text{O}_3$:$0.45\text{-}0.47 \text{ P}_2\text{O}_5$:$0.18\text{-}0.40 \text{ R(OH)}_2$:$30\text{-}50 \text{ H}_2\text{O}$, where R=DiQ-C$_4$ or DiQ-C$_3$. All CIT-16P materials were prepared in 23 cm$^3$ stainless steel autoclaves with experiments with DiQ-C$_3$, ERI competitively formed either as the primary or secondary phase, which prompted us to consider a longer molecule, DiQ-C$_4$, in an attempt to suppress (or eliminate) the formation of ERI. The synthesis results and corresponding PXRD patterns are summarized in Table S1 and FIG. 3.

TABLE S1

Products and gel chemical compositions for the synthesis
of CIT-16P/ERI using DiQ-C$_3$—(OH)$_2$ as an OSDA.

| | Gel Compositions and Synthesis Conditions | | | | | | | Quality of CIT-16p[c] |
|---|---|---|---|---|---|---|---|---|
| Entry | Al$_2$O$_3$[a] | P$_2$O$_5$ | SiO$_2$ | R(OH)$_2$ (DiQ-C$_3$) | H$_2$O | Conditions | XRD[b] | |
| S1 | 0.50 | 0.45 | 0.11 | 0.37 | 40 | 190° C. 72 h/rotation | ERI | — |
| S2 | 0.50 | 0.45 | 0.10 | 0.37 | 40 | 190° C. 72 h/rotation | ERI | — |
| S3 | 0.50 | 0.45 | 0.10 | 0.33 | 40 | 190° C. 72 h/rotation | ERI + impurity | — |
| S4 | 0.50 | 0.45 | 0.12 | 0.27 | 40 | 190° C. 72 h/rotation | CIT-16P + ERI | 2 |
| S5 | 0.50 | 0.45 | 0.10 | 0.27 | 40 | 190° C. 72 h/rotation | CIT-16P + ERI | 2 |
| S6 | 0.50 | 0.45 | 0.08 | 0.27 | 40 | 190° C. 72 h/rotation | CIT-16P + ERI | 2 |
| S7 | 0.50 | 0.45 | 0.10 | 0.24 | 40 | 190° C. 72 h/rotation | CIT-16P + ERI | 2 |
| S8 | 0.50 | 0.45 | 0.06 | 0.24 | 40 | 190° C. 72 h/rotation | CIT-16P + ERI | 3 |
| S9 | 0.50 | 0.45 | 0.10 | 0.21 | 40 | 190° C. 72 h/rotation | CIT-16P + ERI | 2 |
| S10 | 0.50 | 0.45 | 0.06 | 0.21 | 40 | 190° C. 72 h/rotation | CIT-16P + ERI | 2 |
| S11 | 0.50 | 0.45 | 0.10 | 0.18 | 40 | 190° C. 72 h/rotation | ERI + CIT-16P | 1 |
| S12 | 0.50 | 0.45 | 0.06 | 0.18 | 40 | 190° C. 72 h/rotation | ERI + CIT-16P | 1 |

[a]Aluminum source: Barcroft SPI Pharma 0250 ™.
[b]First phase listed is the major phase whereas the second phase listed is the secondary phase.
[c]Refers to the crystallinity of the material formed; 3 indicates best crystallinity and 1 is poorest.

Teflon liners. In a typical synthesis, a desired amount of H$_3$PO$_4$ was mixed with an appropriate amount of water, and the mixture was stirred for 10 mins. Next, the aluminum source (typically, Barcroft™ 0250 dried aluminum hydroxide gel, SPI Pharma) was weighed separately and added to this mixture. This gel was allowed to homogenize for 3-4 hours before adding fumed silica. Following the addition of silica, the OSDA (DiQ-C$_3$ or DiQ-C$_4$) was added, and the gel was aged at room temperature for 20-24 hours before being heated to 180-200° C. in a rotating oven (55-60 rpm) at autogenous pressure for 1-4 days.

The best crystallized CIT-16P materials were prepared using the following gel: $0.03\text{-}0.04 \text{SiO}_2$:$0.47\text{-}0.50 \text{ Al}_2\text{O}_3$ (Barcroft):$0.45 \text{ P}_2\text{O}_5$:$0.27\text{-}0.29 \text{ DiQ-C}_4$—(OH)$_2$:$40\text{H}_2\text{O}$ (190° C., rotating, 1-3 days). Note that even slight deviations in the amounts of Al- or Si-sources, phosphoric acid, water, or DiQ-C$_4$ from the above gel led to the formation of impurities or co-crystallization of CIT-16P with other frameworks (e.g., AFX and SAT). A pure-phase SAPO-17 sample was synthesized according to a method previously reported and used in this work as a reference ERI-type material. See Alshafei, F. H.; Park, Y.; Zones, S. I.; Davis, M. E., Methanol-to-olefins catalysis on ERI-type molecular sieves: towards enhancing ethylene selectivity, *J. Catal.* 2021, 404, 620-633.

CIT-16P was first obtained as an impurity phase during the synthesis of SAPO-17 (ERI) using a gel composition of 0.1 SiO$_2$:0.50 Al$_2$O$_3$ (Barcroft):0.45 P$_2$O$_5$:0.27 DiQ-C$_3$—(OH)$_2$:40 H$_2$O and crystallization conditions of 190° C. for 72 h. Subsequently, it was found that the phase associated with CIT-16P could be enhanced by altering the OSDA concentration and the silicon content (Table S1 and FIG. 3). Specifically, it was observed that the CIT-16P phase dominates the product when the OSDA concentration was in the range of 0.24-0.27 and the silicon content was low (0.06). Further increasing the OSDA or decreasing it outside of the aforementioned range led to the formation of ERI. In all our The results in FIG. 3 show that high OSDA concentration in the gel (0.37) leads to pure SAPO-17 (ERI) formation. However, by decreasing the OSDA concentration, the peaks associated with CIT-16P start to emerge. The peaks are highest when the OSDA concentration is about (0.24-0.27), but they decrease as the OSDA concentration is lowered even further (<0.24). The results also demonstrate that reducing the Si content (by comparing Entry S7 to S8) in the gel while maintaining the OSDA concentration at identical levels enhances the crystallization of CIT-16P, thus, leading to improved peak intensities. Note that the peak intensities associated with ERI were relatively the same irrespective of the gel composition.

A more thorough study on the DiQ-C$_4$ system was performed as shown in Table S2 and FIG. 4, which showed more promise for the synthesis of CIT-16P. The gel compositions within the range of x (0.02-0.12) SiO$_2$: y (0.45-0.50) Al$_2$O$_3$: z (0.45-0.47) P$_2$O$_5$: w (0.27-0.40) R(OH)$_2$: 30-50 H$_2$O at 180-200° C. were tested to crystallize CIT-16P. As mentioned above, similar to the DiQ-C$_3$ system, the DiQ-C$_4$ OSDA crystallized a high-crystallinity CIT-16P phases within a narrow range of gel Si and OSDA contents, preferably x=0.02-0.04 and w=0.27-0.29 at 190° C., respectively. The DiQ-C$_4$ system also featured the co-crystallization of other competing phases (e.g., AFX and SAT with longer or wider ABC-6 cages than ERI) in many tested conditions. These results suggest that the chain length of the diquaternary OSDA impacts the cage size of the impurity phases in the AlPO$_4$ system, as indicated by previous studies. See Castro, M.; et al. Molecular Modeling, Multinuclear NMR, and Diffraction Studies in the Templated Synthesis and Characterization of the Aluminophosphate Molecular Sieve STA-2, *J. Phys. Chem. C* 2010, 114, 12698-12710; Turrina, A.; et al. STA-20: An ABC-6 Zeotype Structure Prepared by Co-Templating and Solved via a Hypothetical Structure Database and STEM-ADF Imaging, *Chem. Mater.*

2017, 29, 2180-2190. Through examining a wide range of conditions, the majority of the AFX and SAT phases were eliminated, and identify a small region of synthesis parameters where CIT-16P forms either as a pure material or a nearly pure material (95+% CIT-16P; abbreviated as 'vs' to indicate that the impurity phase is very small).

SAT phases start to emerge or increase in intensities. SAT and AFX are known to form using DiQ-$C_{4-5}$. The results above also demonstrate that CIT-16P favors gels with low silicon content (0.02-0.04), in agreement with the results on the DiQ-$C_3$ OSDA.

TABLE S2

Products and gel chemical compositions for the synthesis of CIT-16 using DiQ-$C_4$—$(OH)_2$ as an OSDA.

| Entry | Al$_2$O$_3$[a] | P$_2$O$_5$ | SiO$_2$ | R(OH)$_2$ (DiQ-C$_3$) | H$_2$O | Conditions[d] | XRD[b] | Quality of CIT-16P[c] |
|---|---|---|---|---|---|---|---|---|
| | | | | | | | Gel Compositions and Synthesis Conditions | |
| | | | Effect of OSDA Concentration and Silicon Content | | | | | |
| S13 | 0.50 | 0.45 | 0.08 | 0.40 | 40 | 190° C. 72 h/Rot. | CIT-16P + SAT + AFX(vs) | 1 |
| S14 | 0.50 | 0.45 | 0.08 | 0.36 | 40 | 190° C. 72 h/Rot. | CIT-16P + AFX(s) + SAT(vs) | 1 |
| S15 | 0.50 | 0.45 | 0.08 | 0.32 | 40 | 190° C. 72 h/Rot. | CIT-16P + AFX(s) + SAT(vs) | 1 |
| S16 | 0.50 | 0.45 | 0.09 | 0.30 | 40 | 190° C. 72 h/Rot. | CIT-16P + AFX(vs) | 2 |
| S17 | 0.50 | 0.45 | 0.12 | 0.28 | 40 | 190° C. 72 h/Rot. | CIT-16P + SAT + AFX(s) | 2 |
| S18 | 0.50 | 0.45 | 0.10 | 0.28 | 40 | 190° C. 72 h/Rot. | CIT-16P + AFX(s) | 3 |
| S19 | 0.50 | 0.45 | 0.06 | 0.28 | 40 | 190° C. 72 h/Rot. | CIT-16P + AFX(vs) | 3 |
| S20 | 0.50 | 0.45 | 0.04 | 0.28 | 40 | 190° C. 24 h/Rot. | CIT-16P | 3 |
| S21 | 0.50 | 0.45 | 0.04 | 0.28 | 40 | 190° C. 72 h/Rot. | CIT-16P | 3 |
| S22 | 0.50 | 0.45 | 0.03 | 0.28 | 40 | 190° C. 24 h/Rot. | CIT-16P | 3 |
| S23 | 0.50 | 0.45 | 0.03 | 0.28 | 40 | 190° C. 48 h/Rot. | CIT-16P | 3 |
| S24 | 0.50 | 0.45 | 0.03 | 0.28 | 40 | 190° C. 72 h/Rot. | CIT-16P | 3 |
| S25 | 0.50 | 0.45 | 0.02 | 0.28 | 40 | 190° C. 72 h/Rot. | CIT-16P + impurity(s) | 3 |
| S26 | 0.50 | 0.45 | 0.12 | 0.27 | 40 | 190° C. 72 h/Rot. | CIT-16P + SAT(s) + AFX(s) | 2 |
| S27 | 0.50 | 0.45 | 0.11 | 0.27 | 40 | 190° C. 72 h/Rot. | CIT-16P + AFX(vs) | 3 |
| S28 | 0.50 | 0.45 | 0.10 | 0.27 | 40 | 190° C. 72 h/Rot. | CIT-16P + AFX(vs) | 3 |
| S29 | 0.50 | 0.45 | 0.10 | 0.27 | 40 | 190° C. 72 h/Rot. | CIT-16P + AFX(vs) | 3 |
| S30 | 0.50 | 0.45 | 0.10 | 0.27 | 40 | 190° C. 72 h/Rot. | CIT-16P + AFX(vs) | 3 |
| S31 | 0.50 | 0.45 | 0.10 | 0.27 | 40 | 190° C. 72 h/Rot. | CIT-16P + AFX(vs) | 3 |
| S32 | 0.50 | 0.45 | 0.10 | 0.27 | 40 | 190° C. 72 h/Rot. | CIT-16P + AFX(vs) + SAT(vs) | 3 |
| S33 | 0.50 | 0.45 | 0.10 | 0.27 | 40 | 190° C. 72 h/Rot. | CIT-16P + AFX(vs) + SAT(vs) | 3 |
| S34 | 0.50 | 0.45 | 0.09 | 0.27 | 40 | 190° C. 72 h/Rot. | CIT-16P + AFX(vs) | 3 |
| S35 | 0.50 | 0.45 | 0.08 | 0.27 | 40 | 190° C. 72 h/Rot. | CIT-16P + AFX(vs) | 3 |
| S36 | 0.50 | 0.45 | 0.06 | 0.27 | 40 | 190° C. 72 h/Rot. | CIT-16P + AFX(vs) | 3 |
| S37 | 0.50 | 0.45 | 0.10 | 0.24 | 40 | 190° C. 72 h/Rot. | CIT-16P + SAT + AFX(s) | 2 |
| S38 | 0.50 | 0.45 | 0.08 | 0.24 | 40 | 190° C. 72 h/Rot. | CIT-16P + SAT(vs) + AFX(vs) | 2 |
| S39 | 0.50 | 0.45 | 0.06 | 0.24 | 40 | 190° C. 72 h/Rot. | CIT-16P + AFX(vs) | 2 |
| | | | | | | Effect of Temperature | | |
| S40 | 0.50 | 0.45 | 0.10 | 0.27 | 40 | 180° C. 96 h/Rot. | CIT-16P + AFX(vs) | 3 |
| S41 | 0.50 | 0.45 | 0.10 | 0.27 | 40 | 200° C. 72 h/Rot. | CIT-16P + AFX(vs) + SAT(vs) | 3 |
| | | | Effect of Changing Al Source and Manipulating the Al/P, R/P, and R/H2O around the Optimal Conditions | | | | | | |
| S42 | 0.50$^V$ | 0.45 | 0.10 | 0.27 | 40 | 190° C. 72 h/Rot. | CIT-16P + SAT + AFX(vs) | 2 |
| S43 | 0.50$^R$ | 0.45 | 0.10 | 0.27 | 40 | 190° C. 72 h/Rot. | CIT-16P + SAT + AFX(s) | 2 |
| S44 | 0.50$^R$ | 0.47 | 0.10 | 0.27 | 40 | 190° C. 72 h/Rot. | SAT + CIT-16P + AFX(s) | 2 |
| S45 | 0.50 | 0.45 | 0.10 | 0.27 | 30 | 190° C. 72 h/Rot. | CIT-16P + AFX(vs) | 3 |
| S46 | 0.50 | 0.45 | 0.10 | 0.27 | 50 | 190° C. 72 h/Rot. | CIT-16P + AFX(vs) + SAT | 2 |
| S47 | 0.48$^R$ | 0.45 | 0.08 | 0.28 | 40 | 190° C. 72 h/Rot. | CIT-16P + AFX(s) + SAT | 2 |
| S48 | 0.48$^R$ | 0.45 | 0.10 | 0.28 | 40 | 190° C. 72 h/Rot. | CIT-16P + AFX(s) + SAT | 2 |
| S49 | 0.47 | 0.45 | 0.10 | 0.27 | 40 | 190° C. 72 h/Rot. | CIT-16P + AFX(vs) + SAT(vs) | 3 |
| S50 | 0.47 | 0.45 | 0.04 | 0.29 | 40 | 190° C. 72 h/Rot. | CIT-16P + AFX(vs) | 3 |
| S51 | 0.47 | 0.44 | 0.10 | 0.29 | 40 | 190° C. 72 h/Rot. | CIT-16P + SAT + AFX(s) | 2 |
| S52 | 0.46$^P$ | 0.45 | 0.10 | 0.27 | 40 | 190° C. 72 h/Rot. | CIT-16P + SAT + AFX(s) | 2 |
| S54 | 0.46$^P$ | 0.45 | 0.06 | 0.27 | 40 | 190° C. 72 h/Rot. | CIT-16P + SAT + AFX(s) | 2 |
| S54 | 0.45 | 0.45 | 0.10 | 0.27 | 40 | 190° C. 72 h/Rot. | SAT + CIT-16P + AFX(s) | 2 |
| S55 | 0.45$^R$ | 0.45 | 0.10 | 0.28 | 40 | 190° C. 72 h/Rot. | CIT-16P + AFX | 1 |

[a]Aluminum source was Barcroft unless otherwise noted. 'R' indicates Reheis F2000, 'P' = Pfaltz and Bauer, and 'V' = Vista.

[b]First phase is the major phase: "vs" = very small, "s" small, as reference to the secondary or impurity phases

[c]Refers to the crystallinity of the material formed; 3 indicates best crystallinity and 1 is poorest.

[d]'Rot' is short for rotational.

The results in FIG. 4 show that there is an optimal OSDA concentration (similar to the DiQ-$C_3$ system; 0.27-0.29) that allows for the synthesis of CIT-16P with relatively high crystallinity. However, by decreasing the OSDA concentration or increasing it such that the gel OSDA concentration is outside this range, the peaks associated with CIT-16P start to dramatically decrease and peaks associated with AFX and Characterization Powder X-ray diffraction patterns were obtained on a Rigaku MiniFlex II instrument using Cu Kα radiation (λ=1.54184 Å) at a scan rate of 0.3-0.6°/min to determine structure type and purity. Morphology and elemental composition were determined via scanning electron microscopy/energy dispersive spectroscopy (SEM/EDS) on a ZEISS 1550VP instrument equipped with an Oxford X-Max S.D.D. energy dispersive X-ray spectrometer. Atomic ratios (atomic %) were reported as Si/T-atom (where T=Si+Al+P). To determine micropore volume using the t-plot method and detect the presence of mesoporosity, $N_2$-adsorption/desorption experiments were performed on each sample at 77 K in a Quantachrome Autosorb iQ adsorption instrument using a constant-dose method. Prior to adsorption measurements, all thermally treated samples (SAPO-17) were outgassed at 60° C. for 0.5 h, followed by holds of 0.5 h at 120° C. and 6 h at 350° C. (all ramping rates were 1° C./min). In physisorption experiments that were performed on the CIT-16P material (prior to thermal treatment), this outgassing procedure was slightly modified to avoid an inadvertent in-situ structural transformation (from CIT-16P to ERI). As such, the maximum degassing temperature was lowered from 350° C. to 200° C., and the hold time was increased from 6 h to 12 h. Thermogravimetric analysis (TGA) measurements were performed on Perkin Elmer STA 6000. As-synthesized (prior to thermal treatment) or thermally treated samples (0.02-0.06 g) were placed in an alumina crucible and heated at 10° C./min in a flowing stream (0.33 cm³/s) of air to various temperatures. In experiments where the transformation of CIT-16P to SAPO-17 was of interest, samples were first heated in TGA at a heating rate of 5° C./min (unless otherwise noted) in a flowing stream (0.33 cm³/s) of air (zero grade). Once the target temperature was reached, this temperature was held for a desired time (e.g., 0, 2, 5 or 10 minutes). The sample was then rapidly cooled and analyzed via PXRD. Liquid ¹³C NMR spectra were recorded on a Varian INOVA 500 MHz spectrometer. All liquid N.M.R. analyses, involving OSDAs, were performed in deuterium oxide ($D_2O$) or deuterated methanol ($CD_3OD$).

All solid-state, magic-angle spinning nuclear magnetic resonance (MAS NMR) and cross-polarization (CPMAS NMR) spectroscopy experiments were conducted on a Bruker 500 MHz spectrometer and a Bruker 4 mm MAS probe. CPMAS NMR experiments were performed on the as-synthesized CIT-16P-type molecular sieve and on the SAPO-17-like (ERI) material that formed following the removal of the OSDA. ²⁹Si CPMAS NMR spectra were acquired at 99.3 MHz and at a spinning rate of 8 kHz and using a recycle delay time of 6 s and 2 s for as-synthesized and thermally treated samples, respectively. ²⁷Al MAS NMR spectra were acquired at 130.2 MHz and at a spin rate of 13 kHz, a π/18 pulse length of 0.5 μs, and a cycle delay time of 0.5 s. ³¹P MAS NMR spectra were acquired at 202.4 MHz at a spin rate of 12 kHz, a π/2 pulse length of 4 μs, and a cycle delay time of 1000 s (T1~200 s) for the as-synthesized material and 4 s for thermally-treated material. ¹³C solid-state NMR spectra were acquired on the as-synthesized samples at 125.7 MHz at a spin rate of 8 kHz, a C.P. contact time of 0.5 ms, and a cycle delay time of 6 s.

For the purpose of illustrating the characterization of CIT-16P, the material that formed from Entry S50 in Table S2 was selected. While other CIT-16P materials that had a higher degree of purity, this material exhibited a high degree of crystallinity, low Al-rich phases (due to the lower P/Al ratio in the gel), and relatively high silicon content (i.e., higher acid site density), which aided the MTO testing.

The CIT-16P (Entry S50 in Table S2) sample was characterized using a number of techniques, before and after thermal treatment, and the results of these analyses are shown in FIG. 5. The PXRD profiles of the as-synthesized CIT-16P sample and that after the thermal treatment were compared to a reference SAPO-17 (ERI) (FIG. 5(a)). The X-ray powder diffraction pattern of CIT-16P was partly consistent with that of ECNU-38P[20], supporting that the two organic-$AlPO_4$ hybrid materials are nearly isostructural except for the occluded OSDA. The diffraction peaks of CIT-16P were indexed on the basis of the structure solution from the Rietveld refinement (vide infra). It was confirmed that the structure of DiQ-$C_4$ OSDA molecules remain unchanged within the as-synthesized CIT-16P as shown in the ¹³C NMR spectrum (FIG. 6). As a result of the elimination of the OSDA, CIT-16P was completely transformed into an ERI phase with a powder diffraction pattern that is perfectly consistent with the reference SAPO-17 that was prepared by direct synthesis. The 2-theta position of the (100) diffraction peak was shifted from 8.30° to 8.00°, while that of the (002) reflection was shifted from 10.42° to 12.06°, before and after the thermal treatment of as-synthesized CIT-16P, respectively. These shifts indicate that the hexagonal unit cell was stretched along the a-axis and contracted along the c-axis, as a result of the transformation from CIT-16P to SAPO-17, corresponding to ca. 22% reduction in the unit cell volume.

SEM analysis demonstrates that CIT-16P has a morphology vastly different from that of ECNU-38P, presumably due to the differences in the OSDA and crystallization conditions. The DiQ-$C_4$ OSDA for CIT-16P crystallized much larger crystals than the 1,1,6,6-tetramethyl-1,6-diazacyclododecane-1,6-diium (TDDH) OSDA for ECNU-38P. See Duan, Z.; et al. Structural Transformation-Involved Synthesis of Nanosized ERI-Type Zeolite and Its Catalytic Property in the MTO Reaction, *Inorg. Chem.* 2022, 61, 8066-8075. A typical CIT-16P sample had crystal sizes of 1-5 μm and a bullet-like or a rice-grain-like morphology, as seen in the scanning electron micrographs (FIG. 5(c)). This morphology of CIT-16P crystals resembles that of UZM-12 zeolite having an ERI crystal structure despite the compositional difference between zeolites and SAPOs. See Lee, J. H.; et al. Synthesis and Characterization of ERI-Type UZM-12 Zeolites and Their Methanol-to-Olefin Performance, *J. Am. Chem. Soc.* 2010, 132, 12971-12982.

AFX, the primary impurity phase usually encountered in a typical CIT-16P synthesis, has a planar morphology that is distinguishable from CIT-16P (see FIGS. 7(a-c)). See W. Noble, G.; et al. The templated synthesis and structure determination by synchrotron microcrystal diffraction of the novel small pore magnesium aluminophosphate STA-2, *J. Chem. Soc. Dalton. Trans.* 1997, 4485-4490.

The thermogravimetric (TG) measurement of CIT-16P in its as-synthesized form (FIG. 5(d)) showed a continuous mass loss curve extending from 25° C. to 500° C. Due to the continuous nature of the mass loss curve, it was difficult to distinguish between the contribution of water loss and that of OSDA decomposition in this range. By 700° C., approximately 26 percent of the total mass was lost. Considering the crystal structure revealed by the X-ray diffractometry analysis (vide infra), the ideal unit cell formula of as-synthesized CIT-16P assuming a full occupancy of OSDA is $Al_{18}P_{18}O_{72}$ [(DiQ-$C_4$)²⁺(OH⁻)₂], which corresponds to 22.2 percent of OSDA content. The TG result indicated that the extra mass loss (26 compared to 22.2) is likely due to physically adsorbed moisture and/or the structural condensation of the framework.

The coordinations of Al, P, and Si in the as-synthesized CIT-16P and resultant SAPO-17 materials were investigated by solid-state CP/MAS NMR spectroscopy (FIG. 8(a-c)). As-synthesized CIT-16P showed two broad signals in its ²⁷Al MAS NMR spectrum at 41.5 ppm and 7.3 ppm that can be attributed to tetrahedral and pentacoordinated Al species, respectively. See Chang, S.; et al. Three-dimensional crystal structure of novel aluminophosphate PST-5 solved using a powder charge flipping method, *RSC Adv.* 2017, 7, 38631-38638; Lee, J. K.; et al. A Family of Molecular Sieves Containing Framework-Bound Organic Structure-Directing Agents, *Angew. Chem. Int. Ed.* 2015, 54, 11097-11101; Egan, J. M.; et al. Mapping aluminum/phosphorus connectivities in aluminophosphate glasses, *J. Non-Cryst. Solids* 2000, 261, 115-126; Zibrowius, B.; Lohse, U., Multinuclear MAS NMR study of the microporous aluminophosphate AlPO4-17 and the related silicoaluminophosphate SAPO-17, *Solid State NMR* 1992, 1, 137-148. The 7.3 ppm [27]Al signal survived cycles of extensive ethanolamine washing steps (FIG. 9), suggesting that this signal is unlikely from extracrystalline Al-containing species, but rather from Al sites bound within the framework. The population of these non-tetrahedral Al sites is significant in the framework of CIT-16P. See Fenzke, D.; et al. NMR intensity measurements of half-integer quadrupole nuclei, *Chem. Phys. Lett.* 1984, 111, 171-175. This 7.3-ppm[27]Al resonance was not observed in the previously reported ECNU-38P sample, presumably due to different hydroxide-framework interactions. See Duan, Z.; et al. Structural Transformation-Involved Synthesis of Nanosized ERI-Type Zeolite and Its Catalytic Property in the MTO Reaction, *Inorg. Chem.* 2022, 61, 8066-8075. Unlike ECNU-38P, CIT-16P showed no small octahedral Al signal in the region from −20 to 0 ppm. However, this could be due to differences in the amount of hydration between the two materials. After thermal treatment, this 7.3-ppm [27]Al resonance disappears. The resultant [27]Al spectrum of the thermally treated CIT-16P sample was compatible with those of dehydrated SAPO-17. See Duan, Z.; et al. Structural Transformation-Involved Synthesis of Nanosized ERI-Type Zeolite and Its Catalytic Property in the MTO Reaction, *Inorg. Chem.* 2022, 61, 8066-8075; Zibrowius, B.; Lohse, U., Multinuclear MAS NMR study of the microporous aluminophosphate AlPO4-17 and the related silicoaluminophosphate SAPO-17, *Solid State NAMR* 1992, 1, 137-148. Therefore, the 7.3-ppm peak is likely the result of extracoordination of the Al site, which has been confirmed by the structural analysis based on the Rietveld powder pattern refinement of as-synthesized CIT-16P. The $^{27}$Al NMR measurements on the hydration-rehydration cycle study after thermal treatment further confirms that the 7.3-ppm [27]Al signal originates from Al-sites coordinated to intracrystalline $H_2O$ or OH (FIG. 10).

The $^{31}$P MAS NMR spectrum of as-synthesized CIT-16P showed two groups of signals in the regions of −9 to −14 ppm and −20 to −30 ppm, the former, which disappear after thermal treatment, suggests the presence of partially OH-coordinated P-sites.[14] See Chang, S.; Jang, H.-G.; Lee, K.-Y.; Cho, S. J., Three-dimensional crystal structure of novel aluminophosphate PST-5 solved using a powder charge flipping method, *RSC Adv.* 2017, 7, 38631-38638. The thermally treated CIT-16P showed only two resonances at −29.1 and −34.7 ppm in the $^{31}$P NMR spectrum, which is consistent with tetrahedrally connected and dehydrated $AlPO_4$— or SAPO-17 results. See Duan, Z.; et al. Structural Transformation-Involved Synthesis of Nanosized ERI-Type Zeolite and Its Catalytic Property in the MTO Reaction, *Inorg. Chem.* 2022, 61, 8066-8075; Zibrowius, B.; Lohse, U., Multinuclear MAS NMR study of the microporous aluminophosphate AlPO4-17 and the related silicoaluminophosphate SAPO-17, *Solid State NAMR* 1992, 1, 137-148. The single resonance (FIG. 8(*c*)) in the $^{29}$Si CPMAS NMR spectrum at ca. −90 ppm indicates that the Si-sites in the SAPO frameworks of the as-synthesized and thermally treated samples are isolated acid sites (P substitution by Si).

Transformation of CIT-16P to SAPO-17 (ERI)

CIT-16P transforms to SAPO-17 (ERI) upon thermal treatment in air at 580° C. Based on results from a separate ex-situ heating experiment using a TG instrument when taken together with data from powder X-ray diffractometry, it was discovered that the beginning of the CIT-16P-to-SAPO-17 transformation occurs at ca. 500° C. (FIGS. 11(*a*-*b*)). By using a finer temperature increment, it was observed that the transformation of as-synthesized CIT-16P to SAPO-17 took approximately five minutes at 495° C. (FIG. 12). As shown by the data in FIG. 5(*d*), at this temperature (about 500° C.), a large weight loss was observed. It's worth noting that the temperature of the CIT-16P transformation is significantly higher than that of ECNU-38P (<450° C.), may be due to a higher thermal stability of the DiQ-$C_4$ OSDA in CIT-16P compared to the 1,1,6,6-tetramethyl-1,6-diazacyclododecane-1,6-diium (TDDH) OSDA in ECNU-38P. See Duan, Z.; et al. Structural Transformation-Involved Synthesis of Nanosized ERI-Type Zeolite and Its Catalytic Property in the MTO Reaction, *Inorg. Chem.* 2022, 61, 8066-8075.

The removal of OSDA was also attempted by treating the as-synthesized CIT-16P with an ozone flow (26-45 µg $O_3$/cc $O_2$) at 150° C. in order to isolate the inorganic structure at a lower temperature. In the case of a large-pore GME-type CIT-9, one day (24 hours) of ozone treatment at 150° C. was sufficient to remove most of the occluded organics. See Dusselier, M., et al. CIT-9: A Fault-Free Gmelinite Zeolite, *Angew. Chem. Int. Ed.* 2017, 56, 13475-13478. Isolating the inorganic framework in CIT-16P, on the other hand, failed even after a prolonged ozone treatment (1-2 weeks) at the same conditions (26 g $O_3$/cc $O_2$ at 150° C.). The micropore volume measured after 2 weeks of ozone treatment was only 0.037 cc/g (FIG. 11(*e*)). After a 4-week of intensive ozone treatment with an increased ozone level (45 g 03/cc 02 at 150° C.), the organics were mostly eliminated, but the framework completely changed, transforming to SAPO-17, despite ca. 4.8% of DiQ-$C_4$ OSDA surviving this long treatment, as shown by the data in FIGS. 11(*c*-*d*) and FIG. 13. These results support the notion that the presence of OSDA is essential to the conservation of the inorganic framework of CIT-16P.

The aforementioned OSDA removal experiments at various oxidizing conditions and temperatures suggest that the inorganic framework of CIT-16P has a high lattice energy that can initiate the transformation once the OSDA is removed. Calculations were performed on the lattice energies of ERI and CIT-16P frameworks to estimate the lattice energy change associated with the transformation.

The CIT-16P structure from the Rietveld refinement was subject to lattice energy minimization calculations using the General Utility Lattice Program (GULP). See Gale, J. D., GULP: A computer program for the symmetry-adapted simulation of solids, *J. Chem. Soc. Faraday Trans.* 1997, 93, 629-637; Nguyen, C. M.; et al. Physisorption and Chemisorption of Linear Alkenes in Zeolites: A Combined QM-Pot(MP2//B3LYP:GULP)—Statistical Thermodynamics Study, *J. Phys. Chem. C* 2011, 115, 23831-23847; Girard, S.; et al. Computational Prediction of the Phase Transformation of Two As-Synthesized Oxyfluorinated Compounds into the Zeotype CHA Forms, *Angew. Chem. Int. Ed.* 2002, 41, 972-975. All atomic coordinates and cell parameters are optimized to zero force using the Broyden-Fletcher-Goldfarb-Shanno (BFGS) minimization method. Calculations were performed at constant pressure using a zeolite shell model as the potential model in which a Buckingham function was used to describe the short-range interactions and a three-body (bond bending) term was included to accurately model O-T-O angles. A shell model was also used to simulate the polarizability of the oxygen atoms. The Newton-Raphson optimizer was employed during an energy minimization, with maximum function and gradient tolerances of 0.0001 and 0.001 eV $\text{Å}^{-1}$, respectively; the symmetry was constrained and the cell parameters varied. A gradient-norm convergence criterion of 0.001 eV $\text{Å}^{-1}$ was used for all optimizations.

Also, the geometry optimization using DFT method were performed using the Quantum-Espresso code, using the ultrasoft pseudo potential with the Perdew-Burke-Ernzerh of exchange-correlation functional to treat the electronic structure within the generalized gradient approximation to density functional theory. See Giannozzi, P.; et al. QUANTUM ESPRESSO: a modular and open-source software project for quantum simulations of materials, *Journal of Physics: Condensed Matter* 2009, 21, 395502. Plane-wave basis set cutoffs were set to 30 and 420 Ry for the smooth part of the wave functions and the augmented charge, respectively; k-sampling was restricted to the gamma point only.

According to the lattice-energy calculation using GULP (the General Utility Lattice Program Version 6) with the two force fields, *Catlaw and Reaxff*, (Gale, J. D., GULP: A computer program for the symmetry-adapted simulation of solids, *J. Chem. Soc. Faraday Trans.* 1997, 93, 629-637) the transition from CIT-16P to ERI stabilizes the lattice by –0.13 eV per T-atom, which is corresponds to –12.5 kJ $(\text{mol T})^{-1}$. This difference in lattice energy is significant when compared to the values obtained using the same GULP algorithm-based approach for other transformations such as *CTH-to-CFI, which corresponds to –3.56 kJ $(\text{mol T})^{-1}$. See Kang, J. H.; et al. Transformation of Extra-Large Pore Germanosilicate CIT-13 Molecular Sieve into Extra-Large Pore CIT-5 Molecular Sieve, *Chem. Mater.* 2019, 31, 9777-9787. The lattice energy calculation was performed using the Quantum Espresso Program suite, ab-initio density functional theory (DFT) package in which the projector augmented wave pseudopotentials (PAW) is utilized with the PBEsol GGA functional, and the resulting value for the lattice energy difference was comparable.

The details of DFT calculation can be found above. These results are summarized in Table S3.

TABLE S3

Framework energy of ERI and CIT-16P obtained from GULP or DFT calculations.

| Structure | Package | Forcefield/ Pseudopotential | Energy $(eV^1, Ry^2)$ | $\Delta E$ $(eV/T)^3$ |
|---|---|---|---|---|
| ERI | GULP6 | Catlow | –4823.073912 | |
| | | Reaxff6 | –929.603122 | |
| | Quantum Espresso | PAW, GGA-PBEsol | –4693.933504 | |
| CIT-16P | GULP6 | Catlow | –4818.557541 | –0.1255 |
| | | Reaxff6 | –924.2484823 | –0.1487 |
| | Quantum Espresso | PAW, GGA-PBEsol | –4693.514886 | –0.1582 |

[1]GULP6
[2]Quantum Espresso
[3]$\Delta E = E_{ERI} - E_{UNK}$ for per T site

Structure Solution of CIT-16P

Synchrotron diffraction data of CIT-16P was measured using beamlines 9B at the Pohang Accelerator Laboratory (Pohang, Korea) where the wavelength of the highly collimated monochromatic synchrotron radiation was $\lambda=1.5298$ Å. The detector arm of the vertical scan diffractometer consisted of seven sets of Soller slits, flat Ge(111) crystal analyzers, anti-scatter baffles, and scintillation detectors, with each set separated by 20°. Data were obtained on the sample at room temperature in flat-plate mode, with a step size of 0.01° for a scan time of 2 s per step, and overlaps of 2° to the next detector bank over the 2θ range of 5-100°.

Diffraction patterns obtained were indexed using the DICVOLO6 program (Boultif, A.; Louër, D., Powder pattern indexing with the dichotomy method, *J. Appl. Crystallogr.* 2004, 37, 724-731) implemented in the FullProf program suite. See Rodriguez-Carvajal, J., Recent advances in magnetic structure determination by neutron powder diffraction, *Physica B* 1993, 192, 5569. The initial structure of the occluded $DiQ\text{-}C_4\text{---}(OH)_2$ in the pore was obtained by the MM2 method implemented in ChemBio3D. See Dudek, M. J.; Ponder, J. W., Accurate modeling of the intramolecular electrostatic energy of proteins, *Journal of Computational Chemistry* 1995, 16, 791-816. Subsequently, the parallel tempering algorithm implemented in the Free Objects for Crystallography program[5] (Favre-Nicolin, V.; Černý, R., FOX, 'free objects for crystallography': a modular approach to ab initio structure determination from powder diffraction, *J. Appl. Cryst.* 2002, 35, 734-743) was applied to determine the framework structure containing OSDA. Then, profile refinement of the structure model, comprising the framework and the included organic molecules, was performed using the Rietveld method in the JANA2006 package. See Petříček, V.; Dušek, M.; Palatinus, L., Crystallographic Computing System JANA2006: General features, *Zeitschrift für Kristallographie—Crystalline Materials* 2014, 229, 345-352. During Rietveld refinement, a pseudo-Voigt function and microscopic broadening, together with a manually interpolated background, were used to describe the peak shapes. The framework was modeled as completely siliceous. Isotropic displacement parameters for all T atoms were constrained to be equal in order to minimize the number of parameters, as were those of all O atoms, and the TLS method was used to describe the thermal motion of OSDA molecule. The framework T(Al, P)—O distances were soft-restrained to 1.62 Å with the standard uncertainty of 0.005 Å. See Urzhumtsev, A.; et al. TLS from fundamentals to practice, *Crystallography Reviews* 2013, 19, 230-270; Winn, M. D.; et al. Use of TLS parameters to model anisotropic displacements in macromolecular refinement, *Acta Crystallogr.* 2001, 57, 122.

As described above, the structure solution of the as-synthesized CIT-16P was obtained from a powder diffraction method employing powder charge flipping algorithm (pCF). The high resolution diffraction patterns of CIT-16P for the Rietveld refinement (FIG. 14) was measured from a synchrotron radiation source at Pohang Accelerator Laboratory (PAL), Pohang, South Korea. The CIT-16P sample had a small amount of AFX impurity that was also identified based on the diffraction pattern acquired from the in-house X-ray diffractometer as well as SEM analysis. Although the amount of AFX impurity was small, the preliminary attempts for structural solutions using FOCUS and pCF failed due to the presence of impurity peaks which interfered with the correct partitioning of the XRD peaks. The contribution of CIT-16P and AFX phases in the acquired diffraction patterns were analyzed based on a structureless refinement (Le Bail analysis), and the information from this analysis was used to solve for the structure solution of CIT-16P. Initially, each phase was identified by iterative indexing, using the Dicvol06 indexing program implemented in the Fullprof program suite. See Boultif, A.; Louër, D., Indexing of powder diffraction patterns for low-symmetry lattices by the successive dichotomy method, *J. Appl. Cryst.* 1991, 24, 987-993. Subsequently, the structureless refinement of each phase was successfully performed employing Jana2006 program suite. See Petříček, V.; Dušek, M.; Palatinus, L., Crystallographic Computing System JANA2006: General features, *Zeitschrift für Kristallographie—Crystalline Materials* 2014, 229, 345-352. CIT-16P and AFX phases were refined in the P6₃ and P6̄2c space groups first, respectively. The structureless analysis of the resultant XRD patterns resulted in reasonably acceptable R factors ($R_p$=0.0485, $R_{wp}$=0.0728, and $R_{exp}$=0.0829). Finally, to obtain the electron density map from each XRD pattern, the charge flipping method was employed for the structural solution. See Oszlinyi, G.; Süto, A., Ab initio structure solution by charge flipping, *Acta Crystallogr. A* 2004, A60, 134-141.

The configuration of the DiQ-C₄ OSDA molecules within the pore system of CIT-16P phase were determined by utilizing the parallel templating method in which the previously obtained framework was considered as a rigid body and the flexible OSDA molecule was placed in the pore randomly. See Kirkpatrick, S.; et al. Optimization by Simulated Annealing, *Science* 1983, 220, 671-680; Deem, M. W.; Newsam, J. M., Framework crystal structure solution by simulated annealing: test application to known zeolite structures, *J. Am. Chem. Soc.* 1992, 114, 7189-719; Chang, S.; et al. Locating Structure Directing Agent and Al in CHA: Combined Study of Structure Determination of X-Ray Powder Diffraction and Classical Lattice Energy Calculation, *Bull. Korean Chem. Soc.* 2021, 42, 477-482; Park, J. H.; et al. Structural analysis of Cu/Zeolite with controlled Si/Al ratio and the resulting thermal stability, *Catal. Today* 2022. The same procedure was also used to identify the configuration of the organic molecules within the AFX phase, the major impurity. The Rietveld refinements on as-synthesized CIT-16P with a small amount of AFX impurity were performed successfully in the space group of P3 for CIT-16P. The list of atomic locations, the lattice parameters of as-synthesized CIT-16P, and related refinement results are given in Tables S4-7. The electron density distribution of the OSDA molecules within the pores of CIT-16P was obtained based on the difference Fourier method (FIG. 16). The 3D contour maps reveal the locations of atoms of the OSDA molecules. The uncertainty in the positions of the OSDA atoms within CIT-16P (FIG. 16(*a*)) were smaller than that within AFX (FIG. 16(*b*)), which indicates that the OSDA cations are more tightly bound to the framework walls in CIT-16P. This strong interaction between OSDA molecules and framework may be one reason for the difficulty of removing the OSDA from as-synthesized CIT-16P. The visualizations of surfaces of equal electron density (FIG. 16(*c*)) show well-defined positions of carbon atoms of the quinuclidinium end groups that make up the CIT-16P OSDA.

TABLE S4

Lattice parameters and reliability factors obtained from the Rietveld refinement.

| Phase | SG | Structural parameters | | | Reliability factor | | | |
| | | a(Å) | c(Å) | volume(Å³) | GOF | $R_p$(%) | $R_{wp}$(%) | $R_{exp}$(%) |
|---|---|---|---|---|---|---|---|---|
| CIT-16P | P₃ | 12.2899(6) | 16.9714(11) | 2220.0(2) | 1.66 | 8.96 | 12.61 | 7.58 |

TABLE S5

Crystallographic Information File (atomic positions and anisotropic tensors of atoms) of CIT-16P acquired by the Rietveld refinement.

```
data_CIT-16P
_chemical_name_systematic
"CIT-16P"
_chemical formula_sum                    'C66.49 Al18 N8.054 O72 P18'
_cell_length_a                           12.2899(6)
_cell_length_b                           12.2899(6)
_cell_length_c                           16.9714(11)
_cell_angle_alpha                        90
_cell_angle_beta                         90
_cell_angle_gamma                        120
_cell_volume                             2220.0(2)
_symmetry_cell_setting                     trigonal
_symmetry_space_group_name_H-M                  'P 3'
_symmetry_space_group_name_Hall                 'P 3'
_symmetry_Int_Tables_number                     143
loop_
_space_group_symop_id
_space_group_symop_operation_xyz
1    x, y, z
2    −y, x − y, z
3    −x + y, −x, z
loop_
_atom_site_label
_atom_site_type_symbol
_atom_site_fract_x
_atom_site_fract_y
_atom_site_fract_z
_atom_site_adp_type
_atom_site_U_iso_or_equiv
_atom_site_site_symmetry_multiplicity
_atom_site_occupancy
```

TABLE S5-continued

Crystallographic Information File (atomic positions and anisotropic
tensors of atoms) of CIT-16P acquired by the Rietveld refinement.

_atom_site_calc_flag
_atom_site_refinement_flags
_atom_site_disorder_assembly
_atom_site_disorder_group

| | |
|---|---|
| Al1 | Al 0.106(6) 0.389(7) 0.697990(4) Uiso 0.24(4) 3 1 d . . . |
| Al2 | Al 0.325(10) 0.431(8) 0.197960(4) Uiso 0.24(4) 3 1 d . . . |
| Al3 | Al 0.431(10) 0.099(7) 0.375100(4) Uiso 0.24(4) 3 1 d . . . |
| Al4 | Al 0.208(10) 0.295(9) 0.875120(4) Uiso 0.24(4) 3 1 d . . . |
| Al5 | Al 0.307(8) 0.492(9) 0.433920(4) Uiso 0.24(4) 3 1 d . . . |
| Al6 | Al 0.032087 0.466(6) 0.933950(4) Uiso 0.24(4) 3 1 d . . . |
| P1 | P 0.082(7) 0.427(8) 0.510560(3) Uiso 0.027(6) 3 1 d . . . |
| P2 | P 0.264(5) 0.457308 0.010590(3) Uiso 0.027(6) 3 1 d . . . |
| P3 | P −0.079(6) 0.205(5) 0.833333(3) Uiso 0.027(6) 3 1 d . . . |
| P4 | P 0.412(7) 0.344(8) 0.333333(3) Uiso 0.027(6) 3 1 d . . . |
| P5 | P 0.374(6) 0.481(7) 0.774640(3) Uiso 0.027(6) 3 1 d . . . |
| P6 | P 0.155(6) 0.485(7) 0.274610(3) Uiso 0.027(6) 3 1 d . . . |
| O1 | O 0.289769 0.029(5) 0.743482(10) Uiso 0.088(16) 3 1 d . . . |
| O2 | O 0.386(14) 0.347(15) 0.243442(10) Uiso 0.088(16) 3 1 d . . . |
| O3 | O 0.428(13) 0.038(7) 0.465096(10) Uiso 0.088(16) 3 1 d . . . |
| O4 | O 0.275(11) 0.359(7) 0.965126(10) Uiso 0.088(16) 3 1 d . . . |
| O5 | O 0.090(17) 0.524(10) 0.708582(10) Uiso 0.088(16) 3 1 d . . . |
| O6 | 0 0.176(11) 0.412(10) 0.208551(10) Uiso 0.088(16) 3 1 d . . . |
| O7 | O 0.189(8) 0.400(9) 0.499978(10) Uiso 0.088(16) 3 1 d . . . |
| O8 | O 0.080(12) 0.597(6) 0.000006(10) Uiso 0.088(16) 3 1 d . . . |
| O9 | O 0.271(7) 0.447(18) 0.705634(10) Uiso 0.088(16) 3 1 d . . . |
| O10 | O 0.156918 0.567(7) 0.205604(10) Uiso 0.088(16) 3 1 d . . . |
| O11 | O 0.145(17) 0.572(8) 0.502918(10) Uiso 0.088(16) 3 1 d . . . |
| O12 | O 0.125(9) 0.433(15) 0.002944(10) Uiso 0.088(16) 3 1 d . . . |
| O13 | O 0.061(7) 0.280(16) 0.854290(10) Uiso 0.088(16) 3 1 d . . . |
| O14 | O 0.584(11) 0.135(12) 0.354260(10) Uiso 0.088(16) 3 1 d . . . |
| O15 | O 0.053(11) 0.561(7) 0.854286(10) Uiso 0.088(16) 3 1 d . . . |
| O16 | O 0.227(8) 0.512(14) 0.354260(10) Uiso 0.088(16) 3 1 d . . . |
| O17 | O −0.011(17) 0.325(5) 0.885296(10) Uiso 0.088(16) 3 1 d . . . |
| O18 | O 0.340(17) 0.388(18) 0.385260(10) Uiso 0.088(16) 3 1 d. . . |
| O19 | O 0.042(7) 0.392(14) 0.323268(10) Uiso 0.088(16) 3 1 d . . . |
| O20 | O 0.256(7) 0.435(9) 0.823295(10) Uiso 0.088(16) 3 1 d . . . |
| O21 | O 0.271(8) 0.19774 0.854290(10) Uiso 0.088(16) 3 1 d . . . |
| O22 | O 0.395(14) 0.215(10) 0.354260(10) Uiso 0.088(16) 3 1 d . . . |
| O23 | O 0.067(11) 0.404(12) 0.604226(10) Uiso 0.088(16) 3 1 d . . . |
| O24 | O 0.281(13) 0.456(15) 0.104300(10) Uiso 0.088(16) 3 1 d . . . |
| O25 | O 0.333333 0.666667 0.938273(10) Uiso 0.12 1 1 d . . . |
| O26 | O 0.333333 0.666667 0.441489(10) Uiso 0.12 1 1 d . . . |
| O27 | O 0.637614 0.265(16) 0.478058(10) Uiso 0.12 3 1 d . . . |
| O28 | O 0.666667 0.333333 0.458414(10) Uiso 0.12 1 0.0986 d . . . |
| C1 | C 0.252(4) 0.136(5) 0.256446(18) Uani 1.1(2) 3 1.17 d . . . |
| C2 | C 0.160(4) 0.138(5) 0.317836(18) Uani 0.71(16) 3 1.17 d . . . |
| C3 | C 0.188(4) 0.111(5) 0.402296(18) Uani 0.59(18) 3 1.17 d . . . |
| C4 | C 0.182(4) 0.110(5) 0.463946(18) Uani 0.6(2) 3 1.17 d . . . |
| N1 | N 0.228(4) 0.159(5) 0.170846(18) Uani 1.1(2) 3 1.17 d . . . |
| N2 | N 0.134(4) 0.091(5) 0.549056(18) Uani 0.6(4) 3 1.17 d . . . |
| C5 | C 0.154(4) 0.092(5) 0.141796(18) Uani 0.6(3) 3 1.17 d . . . |
| C6 | C 0.168(4) 0.128(5) 0.057206(18) Uani 0.8(4) 3 1.17 d . . . |
| C7 | C 0.199(4) 0.198(5) 0.025316(18) Uani 1.6(5) 3 1.17 d . . . |
| C8 | C 0.308(4) 0.173(5) 0.033556(18) Uani 2.2(6) 3 1.17 d . . . |
| C9 | C 0.233(4) 0.285(5) 0.163256(18) Uani 2.9(5) 3 1.17 d . . . |
| C10 | C 0.227(4) 0.313(5) 0.075586(18) Uani 3.8(8) 3 1.17 d . . . |
| C11 | C 0.333(4) 0.161(5) 0.121066(18) Uani 2.5(5) 3 1.17 d . . . |
| C12 | C 0.240(4) 0.190(5) 0.599396(18) Uani 0.9(4) 3 1.17 d . . . |
| C13 | C 0.201(4) 0.169(5) 0.686606(18) Uani 0.7(6) 3 1.17 d . . . |
| C14 | C 0.265(4) 0.148(5) 0.662856(18) Uani 1.0(6) 3 1.17 d . . . |
| C15 | C 0.252(4) 0.189(5) 0.554816(18) Uani 1.0(3) 3 1.17 d . . . |
| C16 | C 0.285(4) 0.223(5) 0.642136(18) Uani 1.4(5) 3 1.17 d . . . |
| C17 | C 0.505(6) 0.170(6) 0.768256(18) Uani 1.1(2) 3 1.17 d . . . |
| C18 | C 0.625(6) 0.260(6) 0.814516(18) Uani 0.99(17) 3 1.17 d . . . |
| C19 | C 0.601(6) 0.256(6) 0.904316(18) Uani 1.01(17) 3 1.17 d . . . |
| C20 | C 0.722(6) 0.344(6) 0.950766(18) Uani 0.9(2) 3 1.17 d . . . |
| N3 | N 0.521(6) 0.170(6) 0.678476(18) Uani 1.1(3) 3 1.17 d . . . |
| N4 | N 0.705(6) 0.347(6) 1.040176(18) Uani 0.9(3) 3 1.17 d . . . |
| C21 | C 0.554(6) 0.298(6) 0.644086(18) Uani 0.9(4) 3 1.17 d . . . |
| C22 | C 0.574(6) 0.296(6) 0.554736(18) Uani 1.0(5) 3 1.17 d . . . |
| C23 | C 0.536(6) 0.163(6) 0.527406(18) Uani 1.1(6) 3 1.17 d . . . |
| C24 | C 0.401(6) 0.074(6) 0.554486(18) Uani 1.1(6) 3 1.17 d . . . |
| C25 | C 0.622(6) 0.139(6) 0.656776(18) Uani 1.3(4) 3 1.17 d . . . |
| C26 | C 0.622(6) 0.122(6) 0.567036(18) Uani 1.4(6) 3 1.17 d . . . |
| C27 | C 0.395(6) 0.070(6) 0.644916(18) Uani 1.2(4) 3 1.17 d . . . |
| C28 | C 0.833(6) 0.442(6) 1.074006(18) Uani 0.9(4) 3 1.17 d . . . |
| C29 | C 0.826(6) 0.442(6) 1.164346(18) Uani 0.9(6) 3 1.17 d . . . |

TABLE S5-continued

Crystallographic Information File (atomic positions and anisotropic
tensors of atoms) of CIT-16P acquired by the Rietveld refinement.

```
C30              C 0.689(6) 0.362(6) 1.190676(18) Uani 1.0(6) 3 1.17 d . . .
C31              C 0.641(6) 0.226(6) 1.165646(18) Uani 1.3(5) 3 1.17 d . . .
C32              C 0.611(6) 0.390(6) 1.058966(18) Uani 1.0(4) 3 1.17 d . . .
C33              C 0.661(6) 0.219(6) 1.076876(18) Uani 1.2(4) 3 1.17 d . . .
C34              C 0.612(6) 0.411(6) 1.148326(18) Uiso 0.0127 3 1.17 d . . .
loop_
_atom_site_aniso_label
_atom_site_aniso_type_symbol
_atom_site_aniso_U_11
_atom_site_aniso_U_22
_atom_site_aniso_U_33
_atom_site_aniso_U_12
_atom_site_aniso_U_13
_atom_site_aniso_U_23
C1               C 0.0(3) 1.2(2) 1.9(3) 0.1(2) −0.05(19) −0.86(16)
C2               C 0.38(13) 0.1(2) 1.8(3) 0.22(13) 0.67(18) 0.67(15)
C3               C −0.1(2) 0.04(16) 1.8(3) −0.01(16) −0.1(2) −0.06(16)
C4               C −0.1(3) 0.0(3) 1.8(3) 0.0(3) −0.1(2) −0.01(19)
N1               N 0.3(3) 0.4(3) 1.8(3) −0.3(3) 0.6(2) −0.2(2)
N2               N −0.1(4) 0.1(5) 1.8(3) −0.1(4) −0.1(3) 0.6(3)
C5               C 0.0(4) 0.1(4) 1.8(3) 0.1(3) 0.1(3) 0.5(2)
C6               C 0.4(5) 0.2(6) 1.8(3) 0.1(5) 0.6(3) 0.6(3)
C7               C 2.1(6) 0.2(7) 1.8(3) 0.3(6) 1.5(3) 0.7(3)
C8               C 0.1(6) 3.0(9) 1.9(3) −0.4(7) 0.3(3) −1.4(3)
C9               C 5.6(8) 0.2(4) 1.9(3) 0.7(5) 2.5(3) 0.8(2)
C10              C 8.4(13) 0.5(7) 1.9(3) 1.7(8) 3.0(3) 1.2(3)
C11              C 0.1(5) 4.5(9) 1.9(3) 0.4(6) −0.2(3) −2.0(3)
C12              C 0.3(5) 0.1(5) 1.9(3) −0.4(5) 0.7(3) −0.4(3)
C13              C 0.1(7) −0.1(8) 1.8(3) −0.1(7) 0.6(4) 0.0(3)
C14              C −0.1(7) 1.1(8) 1.9(3) 0.1(7) −0.3(4) −1.2(3)
C15              C 0.2(4) 0.3(4) 1.9(3) −0.4(4) 0.6(3) −0.6(2)
C16              C 0.4(6) 0.6(7) 1.9(3) −0.7(6) 0.8(3) −0.9(3)
C17              C 0.0(2) 0.2(2) 3.1(4) 0.0(2) 0.0(3) 0.5(2)
C18              C −0.02(14) 0.15(18) 2.8(3) 0.01(14) 0.2(2) 0.02(19)
C19              C 0.03(14) 0.25(18) 2.8(3) 0.08(14) 0.3(2) 0.52(19)
C20              C 0.1(2) 0.2(2) 2.5(4) 0.1(2) 0.5(3) 0.1(2)
N3               N 0.0(4) 0.1(4) 3.1(4) 0.0(4) −0.1(3) 0.0(3)
N4               N 0.2(4) 0.3(4) 2.5(4) 0.2(4) 0.6(3) 0.5(3)
C21              C 0.2(5) 0.0(5) 2.4(4) 0.0(5) 0.6(3) 0.1(3)
C22              C 0.2(7) 0.0(7) 2.5(3) −0.1(7) 0.5(4) −0.4(3)
C23              C 0.1(8) 0.0(8) 3.2(4) 0.0(8) −0.4(5) −0.7(4)
C24              C 0.1(7) −0.1(7) 3.4(5) 0.0(7) −0.6(5) 0.1(4)
C25              C 0.1(5) 0.3(4) 3.5(4) 0.2(5) −0.8(3) −1.1(3)
C26              C 0.2(8) 0.5(7) 3.6(4) 0.3(7) −1.0(4) −1.5(3)
C27              C 0.0(5) 0.1(5) 3.4(5) −0.1(5) −0.5(4) 0.5(4)
C28              C 0.4(5) 0.2(5) 2.3(5) 0.2(5) 0.8(4) 0.0(4)
C29              C 0.5(7) 0.2(8) 2.3(5) 0.4(7) 0.8(5) 0.4(4)
C30              C 0.5(8) 0.5(7) 2.4(4) 0.5(8) 0.9(5) 1.2(4)
C31              C 0.4(7) 0.4(7) 3.0(3) 0.2(7) 0.0(4) 1.1(3)
C32              C 0.6(5) 0.8(4) 2.1(4) 0.7(4) 1.2(3) 1.4(3)
C33              C 0.3(5) 0.2(5) 3.1(4) 0.1(5) −0.1(3) 0.5(3)
```

TABLE S6

Bond valences and bond distances for specific positions.

Bond valence

| | |
|---|---|
| Al1 | 2.9(4) |
| Al2 | 3.1(6) |
| Al3 | 3.2(6) |
| Al4 | 3.1(5) |
| Al5 | 3.4(6) |
| Al6 | 2.8(3) |
| P1 | 5.0(8) |
| P2 | 4.8(7) |
| P3 | 4.6(5) |
| P4 | 5.1(12) |
| P5 | 4.7(5) |
| P6 | 5.1(6) |

TABLE S6-continued

Bond valences and bond distances for specific positions.

Bond distance for specific position

| | | | |
|---|---|---|---|
| Al5—O7 | 1.73(8) | 2nd: O7 | x, y, z |
| Al5—O11 | 1.76(9) | 2nd: O11#s2t1, 1, 0 | −y + 1, x − y + 1, z |
| Al5—O16 | 1.76(12) | 2nd: O16 | x, y, z |
| Al5—O18 | 1.7(3) | 2nd: O18 | x, y, z |
| Al5—O26 | 2.01(11) | 2nd: O26 | x, y, z |
| P2—O4 | 1.50(11) | 2nd: O4#t0, 0, −1 | x, y, z − 1 |
| P2—O8 | 1.58(12) | 2nd: O8#s2t1, 1, 0 | −y + 1, x − y + 1, z |
| P2—O12 | 1.59(15) | 2nd: O12 | x, y, z |
| P2—O24 | 1.60(3) | 2nd: O24 | x, y, z |
| P2—O25 | 2.581(11) | 2nd: O25#t0, 0, −1 | x, y, z − 1 |

TABLE S7

Topological analysis results for CIT-16P.
Material name CIT-16P
Framework type found Congratulation: you seem to have
a new framework (no existing code was found for your structure)
Number of unique topological T-atoms 3 (out of 3 T-atoms in your structure)

| Atom | type | T-atom[a] | | | | | | Coordination Sequence $N_1$ to $N_{12}$ | | | | | | | Vertex Symbol[b] |
|------|------|--------|---|----|----|----|----|-----|-----|-----|-----|-----|-----|------------------|
| Si1 | Si | T1 | 4 | 10 | 18 | 29 | 47 | 75 | 101 | 121 | 149 | 193 | 240 | 284 | $4 \cdot 6 \cdot 4 \cdot 6 \cdot 6_3 \cdot 10_5$ |
| Si2 | Si | T2 | 4 | 9 | 18 | 32 | 49 | 64 | 86 | 125 | 165 | 195 | 227 | 273 | $4 \cdot 6 \cdot 4 \cdot 10_3 \cdot 4 \cdot 10_4$ |
| Si3 | Si | 73 | 4 | 9 | 17 | 29 | 48 | 71 | 97 | 124 | 150 | 182 | 236 | 297 | $4 \cdot 4 \cdot 4 \cdot 6_2 \cdot 6_2 \cdot 8_2$ |

[a]Topologically equivalent atom positions have the same "T-type" symbol
[b]Size and number of smallest ring on each angle of the T-atom (M. O'Keeffe and S.T. Hyde, *Zeolites* 19, 370 (1997))
* = no closed ring at this angle
[c]A specific Coordination Sequence can also occur in a different framework structure (partial match). This is listed here if it was found for an atom in the submitted structure. The T-atom given refers to the one listed under Framework > List of T-atoms for the given code.

The framework structure of CIT-16P is closely related to that of ERI, which is the final product of the transformation. CIT-16P is composed of a "pre-can" composite building unit (CBU) of a high-strain that transforms into a can unit of ERI as a result of the OSDA removal (FIG. 17(a)). A can CBU is composed of 18 T-atoms of three layers that forms the ABA stacking sequence. In FIG. 17(b), the top (A), middle (B), and bottom (A) layers are visualized in purple, blue and green colors, respectively. Within the pre-can unit of CIT-16P, the top-layer T-atoms are directly connected to the bottom-layer T-atoms via T-O-T (A16-O15-P5) bridges, which may engender a "stress" within the framework. As a result, the connected T-sites (A16 and P5) have O-T-O angles that highly deviate from the tetrahedral angle (109.5°). Furthermore, an extra electron density was observed on the middle of the pre-can cage of CIT-16P, which is identified as an extra oxygen site (O25) in the refined structure (FIG. 17(c)). This oxygen site forms an extra coordination to the closest Al site (A16), which is likely the origin of the pentacoordinated Al-sites observed at 7.3 ppm in the $^{27}$Al NMR spectrum of as-synthesized CIT-16P. The strain generated by the direct connection of the top and bottom layers could be partially stabilized by this extra coordination. The high potential energy of this structural unit is supported by the presence of OSDA molecules within "pre-eri cages" surrounding pre-can units. In this respect, the transformation of CIT-16P into SAPO-17 can be understood as a rearrangement of T-O-T bonds, which forms a stable can unit, triggered by the removal of the OSDA.

Catalytic Testing

Catalyst evaluation was carried out in a fixed-bed reactor at ambient pressure. In a typical experiment, approximately 200 mg of dried catalyst (35-60 mesh size) was loaded between two layers of quartz wool in a 0.25"×6" stainless steel reactor as a part of a BTRS Jr. continuous flow reactor (Parker Autoclave Engineers). The dry weight of the catalyst was estimated on the basis of thermogravimetric analysis (TGA; PerkinElmer STA 6000). The catalyst was first pretreated by heating to 150° C. at 1° C./min, held for 3 hours, and then heated further to 580° C. at 1° C./min and held for 12 h under flowing air (breathing-grade D, AirGas). Methanol was introduced via a liquid syringe pump (Harvard Apparatus Pump 11 Elite) at 4.0-5.0 µL/min into a gas stream of an inert blend (95% He and 5% Ar; G.C. internal standard) at a volumetric flow rate of 30 cm$^3$/min. The methanol flow rate was adjusted, depending on the actual weight of the dried catalyst loaded in the reactor, to achieve a weight hourly space velocity (WHSV) of 1.3 h$^{-1}$. The reaction was performed at a WHSV of 1.3 h$^{-1}$ and a temperature of 400° C. Effluent gases were evaluated using an on-stream Agilent GC-MS (G.C. 6890N/MSD5793N) equipped with a Plot-Q capillary column. Aliquots of product flow were analyzed every 16 minutes. All selectivity values were calculated on a carbon-number basis.

It is known that ERI-type zeolites give improved ethylene-to-propylene ratios (E/P=1.1-1.9) over chabazite (CHA)-based materials such as SSZ-13 and SAPO-34. On the other hand, SAPO-ERI samples (i.e., SAPO-17) produced an E/P of 0.7-1.1 and a generally high $C_{4+}$ fraction. The differences observed in the olefins product distributions between the zeolites with low framework Si/Al and SAPO-17 with low Si/T-atom ratio were the result of slower maturation of aromatic hydrocarbon-pool (HP) species and the presence of aromatics with bulky alkyl-groups ($C_3$-$C_4$) in the SAPO-17 samples, indicating the possibility of a larger contribution from the olefins cycle in SAPO-17 materials with low acid site densities.

The SAPO-17 sample that formed from the transformation of CIT-16P (Entry S50) via thermal treatment in air has a Si/T-atom of 0.022 (as determined by EDS). This is a fairly low Si/T value, and is indeed lower than the lowest value/material previously tested (SAPO-17-1, with a Si/T=0.034). See Alshafei, F. H.; et al. Methanol-to-olefins catalysis on ERI-type molecular sieves: towards enhancing ethylene selectivity, *J. Catal.* 2021, 404, 620-633. FIG. 18 shows the MTO behavior of the SAPO-17 sample obtained from the thermal treatment of CIT-16P (Entry S50). The MTO reaction was conducted at 400° C. and a methanol WHSV of 1.3 h$^{-1}$, as described in the Experimental Section.

The thermally treated CIT-16P material achieves 100% methanol conversion and forms primarily $C_{3+}$ at the early stages of the reaction. However, as the reaction proceeds, the ethylene selectivity improves at the expense of the $C_{3+}$ fraction.[17] The averaged ethylene, propylene, and $C_4$ selectivities achieved on this catalyst when methanol conversion is greater than 97% are 21%, 33%, and 15.2%, respectively. These numbers lead to an E/P of about 0.66, which slightly lower than the E/P achieved by SAPO-17-1 (Si/T=0.034; E/P=0.7) in previous work. See Alshafei, F. H.; et al Methanol-to-olefins catalysis on ERI-type molecular sieves: towards enhancing ethylene selectivity, *J. Catal.* 2021, 404, 620-633. TGA experiments on the coked SAPO-17 sample derived from CIT-16P reveal that the coke content (determined in the temperature range of 300 to 850° C.) is approximately 11.2%.

Because the SAPO-17 catalyst derived from CIT-16P has larger crystal sizes (in the low micron range) than the nanosized ECNU-38 material reported by Wu et al., (Duan, Z.; Wang, N.; Xu, H.; Wu, P., Structural Transformation-Involved Synthesis of Nanosized ERI-Type Zeolite and Its Catalytic Property in the MTO Reaction, *Inorg. Chem.* 2022, 61, 8066-8075), it has a better MTO activity and an extended lifetime. Indeed, ERI-type catalysts that appear to have crystal sizes (<100 nm) deactivate rather rapidly due to the fast buildup of external coke, as was previously observed on nanosized UZM-12 materials, (Lee, J. H.; Park, M. B.; Lee, J. K.; Min, H.-K.; Song, M. K.; Hong, S. B., Synthesis and Characterization of ERI-Type UZM-12 Zeolites and Their Methanol-to-Olefin Performance, *J. Am. Chem. Soc.* 2010, 132, 12971-12982), nanosized ECNU-38, (Duan, Z.; Wang, N.; Xu, H.; Wu, P., Structural Transformation-Involved Synthesis of Nanosized ERI-Type Zeolite and Its Catalytic Property in the MTO Reaction, *Inorg. Chem.* 2022, 61, 8066-8075) and also nanosized ERI-type zeolites in our prior work (ERI-Zeolite-3). See Alshafei, F. H.; et al Methanol-to-olefins catalysis on ERI-type molecular sieves: towards enhancing ethylene selectivity, *J. Catal.* 2021, 404, 620-633. In spite of the improved lifetime achieved here by forming CIT-16P materials with crystal sizes that are more suitable for MTO than ECNU-38, the inherent low silicon content requirement for forming 'pure' CIT-16P invariably leads to the formation of ERI-SAPO materials with low acid site densities. This property leads the catalytic material to form low E/P, in agreement with our previous observations and trends on ERI-type materials.

CONCLUSION

CIT-16P, a SAPO framework that is stabilized by the presence of quinuclidinium-based diquat OSDAs, was synthesized and characterized. CIT-16P was crystallized using two OSDA systems, DiQ-C$_3$ and DiQ-C$_4$, within narrow ranges of synthetic parameters. CIT-16P transformed into SAPO-17, similarly to the recently reported case of ECNU-38P that was synthesized from TDDH. The onset temperature of the transformation of as-synthesized CIT-16P was 490-500° C., which corresponds to the OSDA decomposition temperature based on TG analysis. The CIT-16P structure was also transformed to SAPO-17 as a result of the OSDA removal following an extensive ozone-treatment at a low temperature (150° C.). These observations indicated that the inorganic structure of CIT-16P was preserved without transformation by the presence of the organic cations.

The structure solution of as-synthesized CIT-16P was obtained from the Rietveld refinement of high-resolution powder XRD pattern. The repeating building unit for the inorganic framework structure of CIT-16P was highly distorted can units, where the top and bottom T-sites are directly connected by T-O-T bonds. This high strain of T-sites present within the distorted can units was manifested by the pentacoordination of Al-sites of as-synthesized CIT-16P that was revealed in the $^{27}$Al MAS NMR spectrum. The positions of DiQ-C$_4$ OSDA cations were also determined based on the different Fourier method. The inorganic framework of CIT-16P fixes the atomic positions of the OSDA molecules in a tighter manner than that of the AFX phase, which is the major impurity phase encountered during the synthesis of CIT-16P. A thermally treated CIT-16P sample having Si/T=0.022 showed an MTO behavior that is similar to that of SAPO-17 materials having a low Si content. Due to the crystal size of CIT-16P, which was larger than that of nanocrystalline ECNU-38P, the resultant SAPO-17 catalyst derived from CIT-16 showed longer lifetime and higher initial methanol conversion than that of ECNU-38 (ERI).

What is claimed:

1. A silicoaluminophosphate molecular sieve (referred to as CIT-16P), comprising a silicoaluminophosphate framework with an occluded OSDA that is DiQ-C$_4$ or DiQ-C$_3$, wherein the CIT-16P is characterized by one or more of the following:
   a. a PXRD pattern substantially as shown in FIG. 3 entries S7, S8, or S9;
   b. a PXRD pattern substantially as shown in FIG. 4 entries S15, S16, S17, S18, S21, S24, S25, or S37;
   c. a PXRD pattern substantially as shown in FIG. 5(*a*);
   d. PXRD peaks at five or more of: 8.5±0.2, 10.1±0.2, 10.6±0.2, 13.5±0.2, 15.5±0.2, 16.9±0.2, 17.7±0.2, 18.0±0.2, 18.1±0.2, 19.9±0.2, 22.3±0.2, 22.9±0.2, 24.7±0.2, 25.3±0.2, 27.4±0.2, 29.5±0.2, 29.8±0.2, 30.6±0.2, 30.8±0.2, 32.3±0.2, or 34.8±0.2 degrees 2-θ;
   e. A thermogravimetric profile substantially as shown in FIG. 5(*d*);
   f. a 8 k MAS solid-state $^{13}$C NMR spectrum substantially as shown in FIG. 6;
   g. a $^{27}$Al MAS spectrum substantially as shown in FIG. 8(*a*);
   h. a $^{27}$Al MAS spectrum having peaks at about 41.5 ppm and about 7.3 ppm;
   i. a $^{31}$P MAS spectrum substantially as shown in FIG. 8(*b*);
   j. a $^{31}$P MAS spectrum having peaks at about −9.8, −13.7, −21.4, −23.7, and −28.1 ppm;
   k. a $^{1}$H-$^{29}$Si CPMAS spectrum substantially as shown in FIG. 8(*c*);
   l. A $^{1}$H-$^{29}$Si CPMAS spectrum having peaks at −91.1 ppm;
   m. a crystal structure having the lattice parameters shown in Table S4;
   n. a crystal structure having the atomic positions and anisotropic tensors of atoms substantially as shown in Table S5;
   o. a crystal structure having the topological analysis shown in Table S7; or
   p. a crystal structure having the bond valences and bond distances substantially as shown in Table S6.

2. The CIT-16P of claim 1, wherein the CIT-16P has an Si/T atom ratio from about 0.01 to about 0.08 as determined by EDS elemental analysis, wherein T=Si+Al+P.

3. The CIT-16P of claim 1, wherein the CIT-16P has a pore volume of less than 0.01 cm$^3$/g.

4. A process for making the CIT-16P molecular sieve of claim 1, the process comprising:
   a. preparing a synthesis gel comprising:
      i. water;
      ii. a phosphorus source;
      iii. an aluminum source;
      iv. a silica source; and
      v. an organic structure determining agent (OSDA);
   b. aging the resulting synthesis gel at room temperature;
   c. heating the aged synthesis gel to about 160-200° C.;
   d. washing the resulting CIT-16P powder; and
   e. drying the CIT-16P powder.

5. The process of claim 4, wherein molar ratio of the components of the synthesis gel is 0.02-0.12 SiO$_2$:0.45-0.50 Al$_2$O$_3$:0.45-0.47 P$_2$O$_5$:0.18-0.40 R (OH)$_2$:30-50 H$_2$O, wherein R=the OSDA which is DiQ-C$_4$ or DiQ-C$_3$.

6. The process of claim 4, the process comprising:
   a. preparing a synthesis gel by a process comprising:
      i. mixing a phosphorus source and water, and stirring the resulting mixture for 10 minutes;

ii. adding an aluminum source, and allowing the resulting gel to homogenize for 3-4 hours;

iii. adding a silica source to the mixture;

iv. adding an organic structure determining agent (OSDA);

b. aging the resulting synthesis gel at room temperature for 20-24 hours;

c. heating the aged synthesis gel to about 160-200° C. for about 1-4 days;

d. washing the resulting CIT-16P powder;

e. drying the CIT-16P powder.

7. The process of claim 6, the process comprising:

a. preparing a synthesis gel by a process comprising:

i. mixing phosphoric acid ($H_3PO_4$) (85%) and water, and stirring the resulting mixture for 10 minutes;

ii. adding aluminum hydroxide, and allowing the resulting gel to homogenize for 3-4 hours;

iii. adding fumed silica to the mixture;

iv. adding an organic structure determining agent (OSDA);

b. aging the resulting synthesis gel at room temperature for 20-24 hours;

c. heating the aged synthesis gel to about 160-200° C. for about 1-4 days;

d. washing the resulting CIT-16P powder;

e. drying the CIT-16P powder.

8. The process of claim 4, wherein the OSDA is DiQ-$C_4$.

9. The process of claim 4, wherein the OSDA is DiQ-$C_3$.

10. The process of claim 4, further comprising converting the CIT-16P to SAPO-17 by removing the occluded OSDA from the CIT-16P.

11. The process of claim 4, further comprising heating the CIT-16P at 470-600° C. to convert the CIT-16P to SAPO-17.

12. The process of claim 4, further comprising treating the CIT-16P with ozone to convert the CIT-16P to SAPO-17.

13. The process of claim 12, wherein the CIT-16P is treated with ozone at about 150° C. to convert the CIT-16P to SAPO-17.

14. A SAPO-17 molecular sieve produced by the process of claim 10.

15. The SAPO-17 of claim 14, wherein the SAPO-17 has an Si/T-atom ratio that is less than 0.034 as determined by EDS elemental analysis, wherein T=Si+Al+P.

16. A SAPO-17 molecular sieve having a Si/T-atom ratio that is less than 0.034 as determined by EDS elemental analysis, wherein T=Si+Al+P.

17. The SAPO-17 of claim 16, wherein the Si/T-atom ratio is 0.022.

18. A process for the production of olefins from a methanol-containing feed, the process comprising: passing the methanol-containing feed to a reactor, wherein the reactor comprises a catalyst comprising a SAPO-17 molecular sieve of claim 14, wherein the reactor is operated at reaction conditions sufficient to generate an effluent stream comprising ethylene and propylene in an ethylene to propylene ratio of about 0.66.

19. A process for the production of olefins from a methanol-containing feed, the process comprising: passing the methanol-containing feed to a reactor, wherein the reactor comprises a catalyst comprising a SAPO-17 molecular sieve of claim 14, wherein the reactor is operated at reaction conditions sufficient to generate an effluent stream comprising averaged ethylene, propylene, and $C_4$ selectivities, on a carbon number basis, of 21%, 33%, and 15.2%, respectively, when the methanol conversion is greater than 97%.

20. The process of claim 18, wherein greater than 97% of the methanol in the methanol-containing feed is converted.

* * * * *